US009046535B2

(12) United States Patent
Montgomery

(10) Patent No.: US 9,046,535 B2
(45) Date of Patent: *Jun. 2, 2015

(54) METHODS AND KITS FOR MEASURING VON WILLEBRAND FACTOR

(75) Inventor: Robert Montgomery, Cedarburg, WI (US)

(73) Assignee: BLOODCENTER RESEARCH FOUNDATION, Milwaukee, WI (US)

(*) Notice: Subject to any disclaimer, the term of this patent is extended or adjusted under 35 U.S.C. 154(b) by 250 days.

This patent is subject to a terminal disclaimer.

(21) Appl. No.: 13/421,217

(22) Filed: Mar. 15, 2012

(65) Prior Publication Data

US 2012/0196308 A1 Aug. 2, 2012

Related U.S. Application Data

(63) Continuation of application No. 12/197,057, filed on Aug. 22, 2008, now Pat. No. 8,163,496.

(60) Provisional application No. 60/957,604, filed on Aug. 23, 2007.

(51) Int. Cl.
*C07K 14/00* (2006.01)
*G01N 33/86* (2006.01)
*G01N 33/50* (2006.01)
*C07K 14/745* (2006.01)

(52) U.S. Cl.
CPC .............. *G01N 33/86* (2013.01); *C07K 14/745* (2013.01); *G01N 33/5008* (2013.01); *G01N 2333/705* (2013.01); *G01N 2333/755* (2013.01)

(58) Field of Classification Search
None
See application file for complete search history.

(56) References Cited

U.S. PATENT DOCUMENTS 8,163,496 B2 * 4/2012 Montgomery ................. 435/7.1
8,318,444 B2 * 11/2012 Montgomery ................. 435/7.1
2010/0136589 A1 6/2010 Althaus et al.

FOREIGN PATENT DOCUMENTS

WO 2009/007051 1/2009

OTHER PUBLICATIONS

Enayat et al., Thromb Haemost. Nov. 2012;108(5):946-54. doi: 10.1160/TH12-04-0189. Epub Sep. 26, 2012.*
Tait et al. "Phenotype changes resulting in high-affinity binding of von Willebrand factor to recombinant glycoprotein Ib-IX: analysis of the platelet-type von Willebrand disease mutations". Hemostasis, Thrombosis, and Vascular Biology, 2001 vol. 98, pp. 1812-1818.
Ulrichts et al. "Von Willebrand Factor But Not alpha-Thrombin Binding to Platelet Glycoprotein Ibalpha Is Influenced by the HPA-2 Polymorphism" Arterioscler Thromb Vasc Biol, 2003, vol. 23, pp. 1302-1307.
Dong et al. "Novel Gain-of-function Mutations of Platelet Glycoprotein Ibalpha by Valine Mutagenesis in the Cys(209)-Cys(248) Disulfide Loop" Journal of Biological Chemistry, 2000 vol. 275, pp. 27663-27670.
Yagi et al. "Structural Characterization and Chromosonal Location of the Gene Encoding Human Platelet Glycoprotein Ibbeta" Journal of Biological Chemistry, 1994, vol. 269, pp. 17424-17427.
Hickey et al. "Characterization of the Gene Encoding Human Platelet Glycoprotein IX" Journal of Biological Chemistry, 1993, vol. 268, pp. 3438-3443.
International Search Report mailed Dec. 4, 2008 in related PCT application PCT/US08/74083.

* cited by examiner

*Primary Examiner* — Michael Szperka
(74) *Attorney, Agent, or Firm* — Quarles & Brady, LLP

(57) ABSTRACT

Methods and kits for measuring levels of von Willebrand factor function in a sample without using a platelet aggregation agonist, such as ristocetin, comprising recombinant glycoprotein Ibα having at least two of a G233V, D235Y and M239V mutations and an agent to detect a complex between the recombinant glycoprotein Ibα and von Willebrand factor.

27 Claims, 8 Drawing Sheets

SEQUENCE LISTING

```
<160> NUMBER OF SEQ ID NOS: 11

<210> SEQ ID NO 1
<211> LENGTH: 2463
<212> TYPE: DNA
<213> ORGANISM: Homo sapiens

<400> SEQUENCE: 1
gagagaagga cggagtcgag tggcacccta gaagacgctc tgtgccttcg gaggtctttc      60
tgcctgcctg tcctcatgcc tctcctcctc ttgctgctcc tgctgccaag ccccttacac     120
ccccacccca tctgtgaggt ctccaaagtg gccagccacc tagaagtgaa ctgtgacaag     180
aggaatctga cagcgctgcc tccagacctg ccgaaagaca caaccatcct ccacctgagt     240
```

-continued

```
gagaacctcc tgtacacctt ctccctggca accctgatgc cttacactcg cctcactcag      300
ctgaacctag ataggtgcga gctcaccaag ctccaggtcg atgggacgct gccagtgctg      360
gggaccctgg atctatccca caatcagctg caaagcctgc ccttgctagg gcagacactg      420
cctgctctca ccgtcctgga cgtctccttc aaccggctga cctcgctgcc tcttggtgcc      480
ctgcgtggtc ttggcgaact ccaagagctc tacctgaaag gcaatgagct gaagaccctg      540
cccccagggc tcctgacgcc cacacccaag ctggagaagc tcagtctggc taacaacaac      600
ttgactgagc tccccgctgg gctcctgaat gggctggaga atctcgacac ccttctcctc      660
caagagaact cgctgtatac aataccaaag ggcttttttg ggtcccacct cctgcctttt      720
gcttttctcc acgggaaccc ctggttatgc aactgtgaga tcctctattt tcgtcgctgg      780
ctgcaggaca atgctgaaaa tgtctacgta tggaagcaag gtgtggacgt caaggccatg      840
acctctaatg tggccagtgt gcagtgtgac aattcagaca agtttcccgt ctacaaatac      900
ccaggaaagg ggtgccccac ccttggtgat gaaggtgaca cagacctata tgattactac      960
ccagaagagg acactgaggg cgataaggtg cgtgccacaa ggactgtggt caagttcccc     1020
accaaagccc atacaacccc ctggggtcta ttctactcat ggtccactgc ttctctagac     1080
agccaaatgc cctcctcctt gcatccaaca caagaatcca ctaaggagca gaccacattc     1140
ccacctagat ggaccccaaa tttcacactt cacatggaat ccatcacatt ctccaaaact     1200
ccaaaatcca ctactgaacc aaccccaagc ccgaccacct cagagcccgt cccggagccc     1260
gccccaaaca tgaccaccct ggagcccact ccaagcccga ccaccccaga gcccacctca     1320
gagcccgccc ccagcccgac cacccccgag cccacctcag agcccgcccc cagcccgacc     1380
accccggagc ccaccccaat cccgaccatc gccacaagcc cgaccatcct ggtgtctgcc     1440
acaagcctga tcactccaaa aagcacattt ttaactacca caaacccgt atcactctta      1500
gaatccacca aaaaaaccat ccctgaactt gatcagccac caaagctccg tggggtgctc     1560
caagggcatt tggagagctc cagaaatgac ccttttctcc accccgactt tgctgcctc      1620
ctcccccctgg gcttctatgt cttgggtctc ttctggctgc tctttgcctc tgtggtcctc     1680
atcctgctgc tgagctgggt tgggcatgtg aaaccacagg ccctggactc tggccaaggt     1740
gctgctctga ccacagccac acaaaccaca cacctggagc tgcagagggg acggcaagtg     1800
acagtgcccc gggcctggct gctcttcctt cgaggttcgc ttcccacttt ccgctccagc     1860
ctcttcctgt gggtacggcc taatggccgt gtggggcctc tagtggcagg aaggaggccc     1920
tcagctctga gtcagggtcg tggtcaggac ctgctgagca cagtgagcat taggtactct     1980
ggccacagcc tctgagggtg ggaggtttgg ggaccttgag agaagagcct gtgggctctc     2040
ctattggaat ctagttgggg gttggagggg taaggaacac agggtgatag gggaggggtc     2100
ttagttcctt tttctgtatc agaagccctg tcttcacaac acaggcacac aatttcagtc     2160
ccagccaaag cagaaggggt aatgacatgg acttggcggg gggacaagac aaagctcccg     2220
atgctgcatg gggcgctgcc agatctcacg gtgaaccatt ttggcagaat acagcatggt     2280
tcccacatgc atctatgcac agaagaaaat ctggaaagtg atttatcagg atgtgagcac     2340
tcgttgtgtc tggatgttac aaatatgggt ggttttattt tcttttttccc tgtttagcat     2400
tttctagttt tccactatta ttgtatatta tctgtataat aaaaaataat tttagggttg     2460
gga                                                                    2463
```

<210> SEQ ID NO 2
<211> LENGTH: 639

<212> TYPE: PRT
<213> ORGANISM: Homo sapiens

<400> SEQUENCE: 2

```
Met Pro Leu Leu Leu Leu Leu Leu Leu Pro Ser Pro Leu His Pro
1               5                   10                  15

His Pro Ile Cys Glu Val Ser Lys Val Ala Ser His Leu Glu Val Asn
            20                  25                  30

Cys Asp Lys Arg Asn Leu Thr Ala Leu Pro Pro Asp Leu Pro Lys Asp
            35                  40                  45

Thr Thr Ile Leu His Leu Ser Glu Asn Leu Leu Tyr Thr Phe Ser Leu
    50                  55                      60

Ala Thr Leu Met Pro Tyr Thr Arg Leu Thr Gln Leu Asn Leu Asp Arg
65                  70                  75                  80

Cys Glu Leu Thr Lys Leu Gln Val Asp Gly Thr Leu Pro Val Leu Gly
                85                  90                  95

Thr Leu Asp Leu Ser His Asn Gln Leu Gln Ser Leu Pro Leu Leu Gly
                100                 105                 110

Gln Thr Leu Pro Ala Leu Thr Val Leu Asp Val Ser Phe Asn Arg Leu
            115                 120                 125

Thr Ser Leu Pro Leu Gly Ala Leu Arg Gly Leu Gly Glu Leu Gln Glu
    130                 135                 140

Leu Tyr Leu Lys Gly Asn Glu Leu Lys Thr Leu Pro Pro Gly Leu Leu
145                 150                 155                 160

Thr Pro Thr Pro Lys Leu Glu Lys Leu Ser Leu Ala Asn Asn Asn Leu
                165                 170                 175

Thr Glu Leu Pro Ala Gly Leu Leu Asn Gly Leu Glu Asn Leu Asp Thr
            180                 185                 190

Leu Leu Leu Gln Glu Asn Ser Leu Tyr Thr Ile Pro Lys Gly Phe Phe
    195                 200                 205

Gly Ser His Leu Leu Pro Phe Ala Phe Leu His Gly Asn Pro Trp Leu
210                 215                 220

Cys Asn Cys Glu Ile Leu Tyr Phe Arg Arg Trp Leu Gln Asp Asn Ala
225                 230                 235                 240

Glu Asn Val Tyr Val Trp Lys Gln Gly Val Asp Val Lys Ala Met Thr
                245                 250                 255

Ser Asn Val Ala Ser Val Gln Cys Asp Asn Ser Asp Lys Phe Pro Val
            260                 265                 270

Tyr Lys Tyr Pro Gly Lys Gly Cys Pro Thr Leu Gly Asp Glu Gly Asp
    275                 280                 285

Thr Asp Leu Tyr Asp Tyr Tyr Pro Glu Glu Asp Thr Glu Gly Asp Lys
290                 295                 300

Val Arg Ala Thr Arg Thr Val Val Lys Phe Pro Thr Lys Ala His Thr
305                 310                 315                 320

Thr Pro Trp Gly Leu Phe Tyr Ser Trp Ser Thr Ala Ser Leu Asp Ser
                325                 330                 335

Gln Met Pro Ser Ser Leu His Pro Thr Gln Glu Ser Thr Lys Glu Gln
            340                 345                 350

Thr Thr Phe Pro Pro Arg Trp Thr Pro Asn Phe Thr Leu His Met Glu
    355                 360                 365

Ser Ile Thr Phe Ser Lys Thr Pro Lys Ser Thr Glu Pro Thr Pro
    370                 375                 380

Ser Pro Thr Thr Ser Glu Pro Val Pro Glu Pro Ala Pro Asn Met Thr
385                 390                 395                 400
```

```
Thr Leu Glu Pro Thr Pro Ser Pro Thr Thr Pro Glu Pro Thr Ser Glu
            405                 410                 415

Pro Ala Pro Ser Pro Thr Thr Pro Glu Pro Thr Ser Glu Pro Ala Pro
        420                 425                 430

Ser Pro Thr Thr Pro Glu Pro Thr Pro Ile Pro Thr Ile Ala Thr Ser
            435                 440                 445

Pro Thr Ile Leu Val Ser Ala Thr Ser Leu Ile Thr Pro Lys Ser Thr
        450                 455                 460

Phe Leu Thr Thr Thr Lys Pro Val Ser Leu Leu Glu Ser Thr Lys Lys
465                 470                 475                 480

Thr Ile Pro Glu Leu Asp Gln Pro Pro Lys Leu Arg Gly Val Leu Gln
            485                 490                 495

Gly His Leu Glu Ser Ser Arg Asn Asp Pro Phe Leu His Pro Asp Phe
        500                 505                 510

Cys Cys Leu Leu Pro Leu Gly Phe Tyr Val Leu Gly Leu Phe Trp Leu
        515                 520                 525

Leu Phe Ala Ser Val Val Leu Ile Leu Leu Ser Trp Val Gly His
        530                 535                 540

Val Lys Pro Gln Ala Leu Asp Ser Gly Gln Gly Ala Ala Leu Thr Thr
545                 550                 555                 560

Ala Thr Gln Thr Thr His Leu Glu Leu Gln Arg Gly Arg Gln Val Thr
                565                 570                 575

Val Pro Arg Ala Trp Leu Leu Phe Leu Arg Gly Ser Leu Pro Thr Phe
            580                 585                 590

Arg Ser Ser Leu Phe Leu Trp Val Arg Pro Asn Gly Arg Val Gly Pro
        595                 600                 605

Leu Val Ala Gly Arg Arg Pro Ser Ala Leu Ser Gln Gly Arg Gly Gln
        610                 615                 620

Asp Leu Leu Ser Thr Val Ser Ile Arg Tyr Ser Gly His Ser Leu
625                 630                 635

<210> SEQ ID NO 3
<211> LENGTH: 958
<212> TYPE: DNA
<213> ORGANISM: Homo sapiens

<400> SEQUENCE: 3
agtaagccgg gctgccgtct tctcgccatg ggctccgggc gcgcggggc gctgagctta      60 ctgctcctgc tgctggcccc gccgagccgc ccggccgcag gttgcccggc gccctgtagc     120
tgcgcgggga cgctcgtgga ctgcgggcgc cgcgggctga cttgggcctc gctgccgacc     180
gccttccctg tcgacacaac cgagctggtg ctgaccggca caacctgac ggcgctgccg      240 ccggggctgc tggacgcgct gccgcgcctg cgcaccgcac acctgggcgc caaccctgg     300 cgctgcgact gccgccttgt gccgctgcgc gctggctgg ccggccgccc cgagcgtgcg     360
ccctaccgcg aactgcgttg cgtggcgccc ccagcgctgc gcggccgcct gctgccctat    420
ctggccgagg acgagctgcg cgccgcttgc gctcccggcc cgctctgctg gggggcgctg    480
gcggcgcagt tgcgctgct gggccttggg ctgctgcacg cgttgctgct ggtgctgctg     540
ctgtgccgcc tgcggaggct gcgggcccgg gcccgcgctc gcgccgcagc ccggctgtcg    600
ctgaccgacc cgctggtggc cgagcgagcc ggaaccgacg agtcctgagg agagaaccgg    660
tgcgtcctga ggagagaacc ggcgctgggc aacacgggc tgcaaactcg acaggaccct     720
gcccgagggg ccctcgcgcc aacctggacc ggtccccgcc tcctccgctg cccaatctct    780
```

```
cagacccacc ccacctgcag gcccagacca cgtgggacag aactcctgcc caccctaccc    840
cgagggaggc gaacccgcac ttccaggctt gggaggacca tggggcacaa tgcggtccag    900
accctgctgc gtctcccttc caaactctgg tgctgaataa accttctga tctggtct     958
```

<210> SEQ ID NO 4
<211> LENGTH: 206
<212> TYPE: PRT
<213> ORGANISM: Homo sapiens

<400> SEQUENCE: 4

```
Met Gly Ser Gly Pro Arg Gly Ala Leu Ser Leu Leu Leu Leu Leu
1               5                  10                  15

Ala Pro Pro Ser Arg Pro Ala Ala Gly Cys Pro Ala Pro Cys Ser Cys
                20                  25                  30

Ala Gly Thr Leu Val Asp Cys Gly Arg Arg Gly Leu Thr Trp Ala Ser
                35                  40                  45

Leu Pro Thr Ala Phe Pro Val Asp Thr Thr Glu Leu Val Leu Thr Gly
        50                  55                  60

Asn Asn Leu Thr Ala Leu Pro Pro Gly Leu Leu Asp Ala Leu Pro Ala
65                  70                  75                  80

Leu Arg Thr Ala His Leu Gly Ala Asn Pro Trp Arg Cys Asp Cys Arg
                85                  90                  95

Leu Val Pro Leu Arg Ala Trp Leu Ala Gly Arg Pro Glu Arg Ala Pro
                100                 105                 110

Tyr Arg Asp Leu Arg Cys Val Ala Pro Pro Ala Leu Arg Gly Arg Leu
                115                 120                 125

Leu Pro Tyr Leu Ala Glu Asp Glu Leu Arg Ala Ala Cys Ala Pro Gly
        130                 135                 140

Pro Leu Cys Trp Gly Ala Leu Ala Ala Gln Leu Ala Leu Leu Gly Leu
145                 150                 155                 160

Gly Leu Leu His Ala Leu Leu Leu Val Leu Leu Leu Cys Arg Leu Arg
                165                 170                 175

Arg Leu Arg Ala Arg Ala Arg Ala Arg Ala Ala Arg Leu Ser Leu
                180                 185                 190

Thr Asp Pro Leu Val Ala Glu Arg Ala Gly Thr Asp Glu Ser
        195                 200                 205
```

<210> SEQ ID NO 5
<211> LENGTH: 3493
<212> TYPE: DNA
<213> ORGANISM: Homo sapiens

<400> SEQUENCE: 5

```
agttactttg gagtgcagaa ccatttcaga catgctgagg gggactctac tgtgcgcggt    60
gctcgggctt ctgcgcgccc agcccttccc ctgtccgcca gcttgcaagt gtgtcttccg   120
ggacgccgcg cagtgctcgg ggggcgacgt ggcgcgcatc tccgcgctag gcctgcccac   180
caacctcacg cacatcctgc tcttcggaat gggccgcggc gtcctgcaga gccagagctt   240
cagcggcatg accgtcctgc agcgcctcat gatctccgac agccacattt ccgccgttgc   300
ccccggcacc ttcagtgacc tgataaaact gaaaaccctg aggctgtcgc gcaacaaaat   360
cacgcatctt ccaggtgcgc tgctggataa gatggtgctc ctggagcagt tgttttggga   420
ccacaatgcg ctaaggggca ttgaccaaaa catgttcag aaactggtta acctgcagga     480
gctcgctctg aaccagaatc agctcgattt ccttcctgcc agtctcttca cgaatctgga   540
```

```
gaacctgaag ttgttggatt tatcgggaaa caacctgacc cacctgccca agggggttgct      600 tggagcacag gctaagctcg agagacttct gctccactcg aaccgccttg tgtctctgga       660
ttcggggctg ttgaacagcc tgggcgccct gacggagctg cagttccacc gaaatcacat       720
ccgttccatc gcacccgggg ccttcgaccg gctcccaaac ctcagttctt tgacgctttc       780
gagaaaccac cttgcgtttc tcccctctgc gctctttctt cattcgcaca atctgactct       840
gttgactctg ttcgagaacc cgctggcaga gctcccgggg gtgctcttcg gggagatggg       900
gggcctgcag gagctgtggc tgaaccgcac ccagctgcgc accctgcccg ccgccgcctt       960
ccgcaacctg agccgcctgc ggtacttagg ggtgactctg agcccgcggc tgagcgcgct      1020
tccgcagggc gccttccagg gccttggcga gctccaggtg ctcgccctgc actccaacgg      1080
cctgaccgcc ctccccgacg gcttgctgcg cggcctcggc aagctgcgcc aggtgtccct      1140
gcgccgcaac aggctgcgcg ccctgccccg tgccctcttc cgcaatctca gcagcctgga      1200
gagcgtccag ctcgaccaca accagctgga gaccctgcct ggcgacgtgt ttggggctct      1260
gccccggctg acggaggtcc tgttggggca caactcctgg cgctgcgact gtggcctggg      1320
gcccttcctg gggtggctgc ggcagcacct aggcctcgtg ggcggggaag agccccacg       1380 gtgcgcaggc cctggggcgc acgccggcct gccgctctgg gccctgccgg ggggtgacgc      1440
ggagtgcccg ggcccccggg gcccgcctcc ccgccccgct gcggacagct cctcggaagc      1500
ccctgtccac ccagccttgg ctcccaacag ctcagaaccc tgggtgtggg cccagccggt      1560
gaccacgggg aaaggtcaag atcatagtcc gttctggggg ttttattttc tgcttttagc      1620
tgttcaggcc atgatcaccg tgatcatcgt gtttgctatg attaaaattg gccaactctt      1680
tcgaaaatta atcagagaga gagcccttgg gtaaaccaat gggaaaatct tctaattact      1740
tagaacctga ccagatgtgg ctcggagggg aatccagacc cgctgctgtc ttgctctccc      1800
tcccctcccc actcctcctc tcttcttcct cttctctctc actgccacgc cttccttttcc     1860 ctcctcctcc ccctctccgc tctgtgctct tcattctcac aggcccgcaa cccctcctct      1920
ctgtgtcccc cgcccgttcc tggaaactga gcttgacgtt tgtaaactgt ggttgcctgc      1980
cttccccagc tcccacgcgg gtgtgcgctg acactgccgg gggcgctgga ctgtgttgga      2040
cccatccgtg ctccgctgtg cctggcttgg cgtctggtgg agagagggggc ctcttcagtg     2100 tctactgagt aaggggacag ctccaggccg gggcctgtct cctgcacaga gtaagccggt      2160
aaatgtttgt gaaatcaatg cgtggataaa ggaacacatg ccatccaagt gatgatggct      2220
tttcctggag ggaaaggata ggctgttgct ctatctaatt ttttgttttt gttttttggac     2280 agtctagctc tgtggcccag gctggcgtgc agtgggccgt ctcagttcac tgcagcctcc      2340
gcctcccagg ttcaagtgat tctcatgcct cagcgttctg agtagctggg attagaggcg      2400
tgtgccacta cacccggcta attttttgtac tttttaaagt agagacgggg ctttgccata     2460
ttggcctggc tgatctcaaa ctcctggtct tgaactcctg ccacaagtg atctgcccgc       2520 cttggcctcc caaagtgctg ggattacagg cgtaagccac tacacctggc cctcttcatc      2580
gaattttatt tgagaagtag agctcttgcc attttttccc ttgctccatt tttctcactt      2640
tatgtctctc tgacctatgg gctacttggg agagcactgg actccattca tgcatgagca      2700
ttttcaggat aagcgacttc tgtgaggctg agagaggaag aaaacacgga gccttccctc      2760
caggtgccca gtgtaggtcc agcgtgtttc ctgagcctcc tgtgagtttc cacttgcttt      2820
acatccatgc aacatgtcat tttgaaactg gattgatttg catttcctgg aactctgcca      2880
```

```
cctcatttca caagcattta tggagcagtt aacatgtgac tggtattcat gaatataatg    2940
ataagcttga ttctagttca gctgctgtca cagtctcatt tgttcttcca actgaaagcc    3000
gtaaaacctt tgttgcttta attgaatgtc tgtgcttatg agaggcagtg gttaaaacag    3060
gggctggcga gttgacaact gtgggttcaa atcccagctc taccacttac taactgcatg    3120
ggactttggg taagacacct gcttacattc tctaagcctt ggtttcctga accttaaaac    3180
aggataacat agtacctgct tcgtagagtt tttgtgagaa ttaaaggcaa taaagcatat    3240
aatgacttag cccagcggcc tgcaggcaat acatgttaat gaatgttagc tattattact    3300
aaaggatgag caattattat tggcatcatg atttctaaag aagagctttg agttggtatt    3360
tttctctgtg tataagggta agtccgaact ttctcagact ggaggttaca ttcacatcag    3420
tctgtcttcc cctgcggatg gcctcagccc tgggtggcca gactctgtgc tcacaatcca    3480
gagcaatgga tcc                                                      3493
```

<210> SEQ ID NO 6
<211> LENGTH: 560
<212> TYPE: PRT
<213> ORGANISM: Homo sapiens

<400> SEQUENCE: 6

```
Met Leu Arg Gly Thr Leu Leu Cys Ala Val Leu Gly Leu Leu Arg Ala
1               5                   10                  15

Gln Pro Phe Pro Cys Pro Ala Cys Lys Cys Val Phe Arg Asp Ala
            20                  25                  30

Ala Gln Cys Ser Gly Gly Asp Val Ala Arg Ile Ser Ala Leu Gly Leu
        35                  40                  45

Pro Thr Asn Leu Thr His Ile Leu Leu Phe Gly Met Gly Arg Gly Val
    50                  55                  60

Leu Gln Ser Gln Ser Phe Ser Gly Met Thr Val Leu Gln Arg Leu Met
65                  70                  75                  80

Ile Ser Asp Ser His Ile Ser Ala Val Ala Pro Gly Thr Phe Ser Asp
                85                  90                  95

Leu Ile Lys Leu Lys Thr Leu Arg Leu Ser Arg Asn Lys Ile Thr His
            100                 105                 110

Leu Pro Gly Ala Leu Leu Asp Lys Met Val Leu Leu Glu Gln Leu Phe
        115                 120                 125

Leu Asp His Asn Ala Leu Arg Gly Ile Asp Gln Asn Met Phe Gln Lys
    130                 135                 140

Leu Val Asn Leu Gln Glu Leu Ala Leu Asn Gln Asn Leu Asp Phe
145                 150                 155                 160

Leu Pro Ala Ser Leu Phe Thr Asn Leu Glu Asn Leu Lys Leu Leu Asp
                165                 170                 175

Leu Ser Gly Asn Asn Leu Thr His Leu Pro Lys Gly Leu Leu Gly Ala
            180                 185                 190

Gln Ala Lys Leu Glu Arg Leu Leu Leu His Ser Asn Arg Leu Val Ser
        195                 200                 205

Leu Asp Ser Gly Leu Leu Asn Ser Leu Gly Ala Leu Thr Glu Leu Gln
    210                 215                 220

Phe His Arg Asn His Ile Arg Ser Ile Ala Pro Gly Ala Phe Asp Arg
225                 230                 235                 240

Leu Pro Asn Leu Ser Ser Leu Thr Leu Ser Arg Asn His Leu Ala Phe
                245                 250                 255

Leu Pro Ser Ala Leu Phe Leu His Ser His Asn Leu Thr Leu Leu Thr
```

```
            260                 265                 270
Leu Phe Glu Asn Pro Leu Ala Glu Leu Pro Gly Val Leu Phe Gly Glu
        275                 280                 285
Met Gly Gly Leu Gln Glu Leu Trp Leu Asn Arg Thr Gln Leu Arg Thr
        290                 295                 300
Leu Pro Ala Ala Ala Phe Arg Asn Leu Ser Arg Leu Arg Tyr Leu Gly
305                 310                 315                 320
Val Thr Leu Ser Pro Arg Leu Ser Ala Leu Pro Gln Gly Ala Phe Gln
            325                 330                 335
Gly Leu Gly Glu Leu Gln Val Leu Ala Leu His Ser Asn Gly Leu Thr
        340                 345                 350
Ala Leu Pro Asp Gly Leu Leu Arg Gly Leu Gly Lys Leu Arg Gln Val
        355                 360                 365
Ser Leu Arg Arg Asn Arg Leu Arg Ala Leu Pro Arg Ala Leu Phe Arg
        370                 375                 380
Asn Leu Ser Ser Leu Glu Ser Val Gln Leu Asp His Asn Gln Leu Glu
385                 390                 395                 400
Thr Leu Pro Gly Asp Val Phe Gly Ala Leu Pro Arg Leu Thr Glu Val
            405                 410                 415
Leu Leu Gly His Asn Ser Trp Arg Cys Asp Cys Gly Leu Gly Pro Phe
        420                 425                 430
Leu Gly Trp Leu Arg Gln His Leu Gly Leu Val Gly Gly Glu Pro
        435                 440                 445
Pro Arg Cys Ala Gly Pro Gly Ala His Ala Gly Leu Pro Leu Trp Ala
        450                 455                 460
Leu Pro Gly Gly Asp Ala Glu Cys Pro Gly Pro Arg Gly Pro Pro Pro
465                 470                 475                 480
Arg Pro Ala Ala Asp Ser Ser Ser Glu Ala Pro Val His Pro Ala Leu
            485                 490                 495
Ala Pro Asn Ser Ser Glu Pro Trp Val Trp Ala Gln Pro Val Thr Thr
        500                 505                 510
Gly Lys Gly Gln Asp His Ser Pro Phe Trp Gly Phe Tyr Phe Leu Leu
        515                 520                 525
Leu Ala Val Gln Ala Met Ile Thr Val Ile Ile Val Phe Ala Met Ile
        530                 535                 540
Lys Ile Gly Gln Leu Phe Arg Lys Leu Ile Arg Glu Arg Ala Leu Gly
545                 550                 555                 560

<210> SEQ ID NO 7
<211> LENGTH: 900
<212> TYPE: DNA
<213> ORGANISM: Homo sapiens

<400> SEQUENCE: 7 gccaggaccct ttcaggccag acaggagcac ctgaccaaag gcttcacagc cgccctcacc      60
gcccggcctt ctacggtgtc cagagacagt tagccaggcc tgggctgggc acactccacc     120
ttccctagtc accagctggt ttcccagagg agaaggctga ccccgagaa gggagccagc      180 ctgtcccatg cctgcctggg gagccctgtt cctgctctgg ccacagcag aggccaccaa      240 ggactgcccc agcccatgta cctgccgcgc cctggaaacc atggggctgt ggtggactg      300 caggggccac ggactcacgg ccctgcctgc cctgccggcc cgcacccgcc accttctgct     360
ggccaacaac agccttcagt ccgtgccccc gggagccttt gaccacctgc ccagctgca     420 gaccctcgat gtgacgcaga accctggca ctgtgactgc agcctcacct atctgcgcct     480
```

```
ctggctggag accgcacgc ccgaggccct gctgcaggtc cgctgtgcca gccccagcct      540
cgctgcccat ggcccgctgg gccggctgac aggctaccag ctgggcagct gtggctggca      600
gctgcaggcg tcctgggtgc gcccgggggt cttgtgggac gtggcgctgg tcgccgtggc      660
cgcgctgggc ctggctcttc tggctggcct gctgtgtgcc accacagagg ccctggattg      720
agccaggccc ccagaacccc tggctccagg ccagggggcc agtccctgag gcaggtcccc      780
agactccacc aagcctggtc agcccaaacc accagaagcc cagaataaac tggcagctca      840
gctgttttat ataaaaaaaa aaaaaaaaaa aaaaaaaaaa aaaaaaaaaa aaaaaaaaaa      900
```

<210> SEQ ID NO 8
<211> LENGTH: 177
<212> TYPE: PRT
<213> ORGANISM: Homo sapiens

<400> SEQUENCE: 8

```
Met Pro Ala Trp Gly Ala Leu Phe Leu Leu Trp Ala Thr Ala Glu Ala
1               5                   10                  15

Thr Lys Asp Cys Pro Ser Pro Cys Thr Cys Arg Ala Leu Glu Thr Met
            20                  25                  30

Gly Leu Trp Val Asp Cys Arg Gly His Gly Leu Thr Ala Leu Pro Ala
        35                  40                  45

Leu Pro Ala Arg Thr Arg His Leu Leu Leu Ala Asn Asn Ser Leu Gln
    50                  55                  60

Ser Val Pro Pro Gly Ala Phe Asp His Leu Pro Gln Leu Gln Thr Leu
65                  70                  75                  80

Asp Val Thr Gln Asn Pro Trp His Cys Asp Cys Ser Leu Thr Tyr Leu
                85                  90                  95

Arg Leu Trp Leu Glu Asp Arg Thr Pro Glu Ala Leu Leu Gln Val Arg
            100                 105                 110

Cys Ala Ser Pro Ser Leu Ala Ala His Gly Pro Leu Gly Arg Leu Thr
        115                 120                 125

Gly Tyr Gln Leu Gly Ser Cys Gly Trp Gln Leu Gln Ala Ser Trp Val
    130                 135                 140

Arg Pro Gly Val Leu Trp Asp Val Ala Leu Val Ala Val Ala Ala Leu
145                 150                 155                 160

Gly Leu Ala Leu Leu Ala Gly Leu Leu Cys Ala Thr Thr Glu Ala Leu
                165                 170                 175

Asp
```

<210> SEQ ID NO 9
<211> LENGTH: 8833
<212> TYPE: DNA
<213> ORGANISM: Homo sapiens

<400> SEQUENCE: 9

```
agctcacagc tattgtggtg ggaaagggag ggtggttggt ggatgtcaca gcttgggctt       60
tatctccccc agcagtgggg actccacagc ccctgggcta cataacagca agacagtccg      120
gagctgtagc agacctgatt gagcctttgc agcagctgag agcatggcct agggtggggcg     180 gcaccattgt ccagcagctg agtttcccag ggaccttgga gatagccgca gccctcattt      240 gcagggaag atgattcctg ccagatttgc cggggtgctg cttgctctgg ccctcatttt       300
gccagggacc ctttgtgcag aaggaactcg cggcaggtca tccacggccc gatgcagcct     360
tttcggaagt gacttcgtca acacctttga tgggagcatg tacagctttg cgggatactg      420
```

```
cagttacctc ctggcagggg gctgccagaa acgctccttc tcgattattg gggacttcca    480
gaatggcaag agagtgagcc tctccgtgta tcttggggaa ttttttgaca tccatttgtt    540
tgtcaatggt accgtgacac agggggacca aagagtctcc atgccctatg cctccaaagg    600
gctgtatcta gaaactgagg ctgggtacta caagctgtcc ggtgaggcct atggctttgt    660
ggccaggatc gatggcagcg gcaactttca gtcctgctg tcagacagat acttcaacaa     720
gacctgcggg ctgtgtggca actttaacat ctttgctgaa gatgacttta tgacccaaga    780
agggaccttg acctcggacc cttatgactt tgccaactca tgggctctga gcagtggaga    840
acagtggtgt gaacgggcat ctcctcccag cagctcatgc aacatctcct ctggggaaat    900
gcagaagggc ctgtgggagc agtgccagct tctgaagagc acctcggtgt tgcccgctg     960 ccaccctctg gtggaccccg agccttttgt ggccctgtgt gagaagactt tgtgtgagtg    1020
tgctgggggg ctggagtgcg cctgccctgc cctcctggag tacgcccgga cctgtgccca    1080
ggagggaatg gtgctgtacg gctggaccga ccacagcgcg tgcagcccag tgtgccctgc    1140
tggtatggag tataggcagt gtgtgtcccc ttgcgccagg acctgccaga gcctgcacat    1200
caatgaaatg tgtcaggagc gatgcgtgga tggctgcagc tgccctgagg acagctcct    1260 ggatgaaggc ctctgcgtgg agagcaccga gtgtcctgc gtgcattccg gaaagcgcta    1320
ccctcccggc acctccctct ctcgagactg caacacctgc atttgccgaa acagccagtg    1380
gatctgcagc aatgaagaat gtccagggga gtgccttgtc acaggtcaat cacacttcaa    1440
gagctttgac aacagatact tcaccttcag tgggatctgc cagtacctgc tggcccggga    1500
ttgccaggac cactccttct ccattgtcat tgagactgtc cagtgtgctg atgaccgcga    1560
cgctgtgtgc acccgctccg tcaccgtccg gctgcctggc ctgcacaaca gccttgtgaa    1620
actgaagcat ggggcaggag ttgccatgga tggccaggac gtccagctcc ccctcctgaa    1680
aggtgacctc cgcatccagc atacagtgac ggcctccgtg cgcctcagct acggggagga    1740
cctgcagatg gactgggatg ccgcgggag gctgctggtg aagctgtccc ccgtctatgc    1800
cgggaagacc tgcggcctgt gtgggaatta caatggcaac cagggcgacg acttccttac    1860
cccctctggg ctggcggagc cccgggtgga ggacttcggg aacgcctgga agctgcacgg    1920
ggactgccag gacctgcaga agcagcacag cgatccctgc gccctcaacc cgcgcatgac    1980
caggttctcc gaggaggcgt gcgcggtcct gacgtccccc acattcgagg cctgccatcg    2040
tgccgtcagc ccgctgccct acctgcggaa ctgccgctac gacgtgtgct cctgctcgga    2100
cggccgcgag tgcctgtgcg gcgccctggc cagctatgcc gcggcctgcg cggggagagg    2160
cgtgcgcgtc gcgtggcgcg agccaggccg ctgtgagctg aactgcccga aaggccaggt    2220
gtacctgcag tgcgggaccc cctgcaacct gacctgccgc tctctctctt acccggatga    2280
ggaatgcaat gaggcctgcc tggagggctg cttctgcccc ccagggctct acatggatga    2340 gagggggac tgcgtgccca aggcccagtc cccctgttac tatgacgtg agatcttcca     2400 gccagaagac atcttctcag accatcacac catgtgctac tgtgaggatg gcttcatgca    2460
ctgtaccatg agtggagtcc ccggaagctt gctgcctgac gctgtcctca gcagtcccct    2520
gtctcatcgc agcaaaagga gcctatcctg tcggcccccc atggtcaagc tggtgtgtcc    2580
cgctgacaac ctgcgggctg aagggctcga gtgtaccaaa acgtgccaga actatgacct    2640
ggagtgcatg agcatgggct gtgtctctgg ctgcctctgc cccccgggca tggtccggca    2700
tgagaacaga tgtgtggccc tggaaaggtg tcctgcttc catcagggca aggagtatgc    2760
```

```
ccctggagaa acagtgaaga ttggctgcaa cacttgtgtc tgtcgggacc ggaagtggaa    2820
ctgcacagac catgtgtgtg atgccacgtg ctccacgatc ggcatggccc actacctcac    2880
cttcgacggg ctcaaatacc tgttccccgg ggagtgccag tacgttctgg tgcaggatta    2940
ctgcggcagt aaccctggga cctttcggat cctagtgggg aataagggat gcagccaccc    3000
ctcagtgaaa tgcaagaaac gggtcaccat cctggtggag ggaggagaga ttgagctgtt    3060
tgacggggag gtgaatgtga agaggcccat gaaggatgag actcactttg aggtggtgga    3120
gtctggccgg tacatcattc tgctgctggg caaagccctc tccgtggtct gggaccgcca    3180
cctgagcatc tccgtggtcc tgaagcagac ataccaggag aaagtgtgtg gcctgtgtgg    3240
gaattttgat ggcatccaga acaatgacct caccagcagc aacctccaag tggaggaaga    3300
ccctgtggac tttgggaact cctggaaagt gagctcgcag tgtgctgaca ccagaaaagt    3360
gcctctggac tcatcccctg ccacctgcca taacaacatc atgaagcaga cgatggtgga    3420
ttcctcctgt agaatcctta ccagtgacgt cttccaggac tgcaacaagc tggtggaccc    3480
cgagccatat ctggatgtct gcatttacga cacctgctcc tgtgagtcca ttggggactg    3540
cgcctgcttc tgcgacacca ttgctgccta tgcccacgtg tgtgcccagc atggcaaggt    3600
ggtgacctgg aggacgggcca cattgtgccc ccagagctgc gaggagagga atctccggga    3660
gaacgggtat gagtgtgagt ggcgctataa cagctgtgca cctgcctgtc aagtcacgtg    3720
tcagcaccct gagccactgg cctgccctgt gcagtgtgtg gagggctgcc atgcccactg    3780
ccctccaggg aaaatcctgg atgagctttt gcagacctgc gttgaccctg aagactgtcc    3840
agtgtgtgag gtggctggcc ggcgtttgc ctcaggaaag aaagtcacct tgaatcccag    3900
tgaccctgag cactgccaga tttgccactg tgatgttgtc aacctcacct gtgaagcctg    3960
ccaggagccg ggaggcctgg tggtgcctcc cacagatgcc ccggtgagcc ccaccactct    4020
gtatgtggag gacatctcgg aaccgccgtt gcacgatttc tactgcagca ggctactgga    4080
cctggtcttc ctgctggatg gctcctccag gctgtccgag gctgagtttg aagtgctgaa    4140
ggcctttgtg gtggacatga tggagcggct gcgcatctcc cagaagtggg tccgcgtggc    4200
cgtggtggag taccacgacg gctccccacg ctacatcggg ctcaaggacc ggaagcgacc    4260
gtcagagctg cggcgcattg ccagccaggt gaagtatgcg ggcagccagg tggcctccac    4320
cagcgaggtc ttgaaataca cactgttcca aatcttcagc aagatcgacc gccctgaagc    4380
ctcccgcatc accctgctcc tgatggccag ccaggagccc caacggatgt cccggaactt    4440
tgtccgctac gtccagggcc tgaagaagaa gaaggtcatt gtgatcccgg tgggcattgg    4500
gccccatgcc aacctcaagc agatccgcct catcgagaag caggcccctg agaacaaggc    4560
cttcgtgctg agcagtgtgg atgagctgga gcagcaaagg gacgagatcg ttagctacct    4620
ctgtgacctt gccctgaag ccctcctcc tactctgccc ccgacatgg cacaagtcac    4680 tgtgggcccg gggctcttgg gggtttcgac cctggggccc aagaggaact ccatggttct    4740
ggatgtggcg ttcgtcctgg aaggatcgga caaaattggt gaagccgact tcaacaggag    4800
caaggagttc atggaggagg tgattcagcg gatggatgtg ggccaggaca gcatccacgt    4860
cacggtgctg cagtactcct acatggtgac tgtggagtac cccttcagcg aggcacagtc    4920 caaagggac atcctgcagc gggtgcgaga gatccgctac cagggcggca acaggaccaa    4980
cactgggctg gccctgcggt acctctctga ccacagcttc ttggtcagcc agggtgaccg    5040
ggagcaggcg cccaacctgg tctacatggt caccggaaat cctgcctctg atgagatcaa    5100
gaggctgcct ggagacatcc aggtggtgcc cattggagtg ggccctaatg ccaacgtgca    5160
```

```
ggagctggag aggattggct ggcccaatgc ccctatcctc atccaggact ttgagacgct    5220 ccccgagag gctcctgacc tggtgctgca gaggtgctgc tccggagagg gctgcagat     5280 ccccaccctc tcccctgcac ctgactgcag ccagccctg  acgtgatcc ttctcctgga    5340 tggctcctcc agtttcccag cttcttattt tgatgaaatg aagagtttcg ccaaggcttt    5400
catttcaaaa gccaatatag ggcctcgtct cactcaggtg tcagtgctgc agtatggaag    5460
catcaccacc attgacgtgc catggaacgt ggtcccggag aaagcccatt tgctgagcct    5520
tgtggacgtc atgcagcggg agggaggccc cagccaaatc ggggatgcct gggctttgc     5580 tgtgcgatac ttgacttcag aaatgcatgg tgccaggccg ggagcctcaa aggcggtggt    5640
catcctggtc acggacgtct ctgtggattc agtggatgca gcagctgatg ccgccaggtc    5700
caacagagtg acagtgttcc ctattggaat tggagatcgc tacgatgcag cccagctacg    5760
gatcttggca ggcccagcag gcgactccaa cgtggtgaag ctccagcgaa tcgaagacct    5820
ccctaccatg gtcaccttgg gcaattcctt cctccacaaa ctgtgctctg atttgttag     5880 gatttgcatg gatgaggatg ggaatgagaa gaggcccggg gacgtctgga ccttgccaga    5940
ccagtgccac accgtgactt gccagccaga tggccagacc ttgctgaaga gtcatcgggt    6000
caactgtgac cggggggctga ggccttcgtg ccctaacagc cagtcccctg ttaaagtgga   6060
agagacctgt ggctgccgct ggacctgccc ctgcgtgtgc acaggcagct ccactcggca    6120
catcgtgacc tttgatgggc agaatttcaa gctgactggc agctgttctt atgtcctatt    6180
tcaaaacaag gagcaggacc tggaggtgat tctccataat ggtgcctgca gccctggagc    6240
aaggcagggc tgcatgaaat ccatcgaggt gaagcacagt gccctctccg tcgagctgca    6300
cagtgacatg gaggtgacgg tgaatgggag actggtctct gttccttacg tgggtgggaa    6360
catggaagtc aacgtttatg gtgccatcat gcatgaggtc agattcaatc accttggtca    6420
catcttcaca ttcactccac aaaacaatga gttccaactg cagctcagcc caagactttt    6480
tgcttcaaag acgtatggtc tgtgtgggat ctgtgatgag aacggagcca atgacttcat    6540
gctgagggat ggcacagtca ccacagactg gaaaacactt gttcaggaat ggactgtgca    6600
gcggccaggg cagacgtgcc agcccatcct ggaggagcag tgtcttgtcc ccgacagctc    6660
ccactgccag gtcctcctct taccactgtt tgctgaatgc cacaaggtcc tggctccagc    6720
cacattctat gccatctgcc agcaggacag ttgccaccag gagcaagtgt gtgaggtgat    6780
cgcctcttat gcccacctct gtcggaccaa cggggtctgc gttgactgga ggacacctga    6840
tttctgtgct atgtcatgcc caccatctct ggtctacaac cactgtgagc atggctgtcc    6900
ccggcactgt gatggcaacg tgagctcctg tggggaccat ccctccgaag gctgtttctg    6960
ccctccagat aaagtcatgt ggaaggcag  ctgtgtccct gaagaggcct gcactcagtg    7020
cattggtgag gatggagtcc agcaccagtt cctggaagcc tgggtcccgg accaccagcc    7080
ctgtcagatc tgcacatgcc tcagcgggcg aaggtcaac  tgcacaacgc agccctgccc    7140
cacggccaaa gctcccacgt gtggcctgtg tgaagtagcc cgcctccgcc agaatgcaga    7200
ccagtgctgc ccccgagtatg agtgtgtgtg tgacccagtg agctgtgacc tgccccccagt    7260 gcctcactgt gaacgtggcc tccagcccac actgaccaac cctggcgagt gcagaccccaa    7320 cttcacctgc gcctgcagga aggaggagtg caaaagagtg tccccacccct cctgcccccc    7380 gcaccgtttg cccaccctttc ggaagaccca gtgctgtgat gagtatgagt gtgcctgcaa    7440
ctgtgtcaac tccacagtga gctgtcccct tgggtacttg gcctcaactg ccaccaatga    7500
```

-continued

```
ctgtggctgt accacaacca cctgccttcc cgacaaggtg tgtgtccacc gaagcaccat    7560
ctaccctgtg ggccagttct gggaggaggg ctgcgatgtg tgcacctgca ccgacatgga    7620
ggatgccgtg atgggcctcc gcgtggccca gtgctcccag aagccctgtg aggacagctg    7680
tcggtcgggc ttcacttacg ttctgcatga aggcgagtgc tgtggaaggt gcctgccatc    7740
tgcctgtgag gtggtgactg gctcaccgcg ggggactcc cagtcttcct ggaagagtgt     7800
cggctcccag tgggcctccc ggagaaccc ctgcctcatc aatgagtgtg tccgagtgaa      7860
ggaggaggtc tttatacaac aaaggaacgt ctcctgcccc cagctggagg tccctgtctg    7920
cccctcgggc tttcagctga ctgtaagac ctcagcgtgc tgcccaagct gtcgctgtga     7980
gcgcatggag gcctgcatgc tcaatggcac tgtcattggg cccgggaaga ctgtgatgat    8040
cgatgtgtgc acgacctgcc gctgcatggt gcaggtgggg gtcatctctg gattcaagct    8100
ggagtgcagg aagaccacct gcaaccctg ccccctgggt tacaaggaag aaaataacac      8160
aggtgaatgt tgtgggagat gttttgcctac ggcttgcacc attcagctaa gaggaggaca   8220
gatcatgaca ctgaagcgtg atgagacgct ccaggatggc tgtgatactc acttctgcaa    8280
ggtcaatgag agaggagagt acttctggga agagggtc acaggctgcc cacccttga       8340 tgaacacaag tgtctggctg agggaggtaa aattatgaaa attccaggca cctgctgtga    8400
cacatgtgag gagcctgagt gcaacgacat cactgccagg ctgcagtatg tcaaggtggg    8460
aagctgtaag tctgaagtag aggtggatat ccactactgc cagggcaaat gtccagcaa     8520 agccatgtac tccattgaca tcaacgatgt gcaggaccag tgctcctgct gctctccgac    8580
acggacggag cccatgcagg tggccctgca ctgcaccaat ggctctgttg tgtaccatga    8640
ggttctcaat gccatggagt gcaaatgctc ccccaggaag tgcagcaagt gaggctgctg    8700
cagctgcatg ggtgcctgct gctgcctgcc ttggcctgat ggccaggcca gagtgctgcc    8760
agtcctctgc atgttctgct cttgtgccct tctgagccca caataaaggc tgagctctta    8820
tcttgcaaaa ggc                                                       8833
```

<210> SEQ ID NO 10
<211> LENGTH: 2813
<212> TYPE: PRT
<213> ORGANISM: Homo sapiens

<400> SEQUENCE: 10

```
Met Ile Pro Ala Arg Phe Ala Gly Val Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
    65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
                100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
```

```
             130                 135                 140
Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Ser Ser
            195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
                260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560
```

```
Asp Leu Gln Lys Gln His Ser Asp Pro Cys Ala Leu Asn Pro Arg Met
            565                 570                 575
Thr Arg Phe Ser Glu Glu Ala Cys Ala Val Leu Thr Ser Pro Thr Phe
            580                 585                 590
Glu Ala Cys His Arg Ala Val Ser Pro Leu Pro Tyr Leu Arg Asn Cys
            595                 600                 605
Arg Tyr Asp Val Cys Ser Cys Ser Asp Gly Arg Glu Cys Leu Cys Gly
            610                 615                 620
Ala Leu Ala Ser Tyr Ala Ala Cys Ala Gly Arg Gly Val Arg Val
625                 630                 635                 640
Ala Trp Arg Glu Pro Gly Arg Cys Glu Leu Asn Cys Pro Lys Gly Gln
            645                 650                 655
Val Tyr Leu Gln Cys Gly Thr Pro Cys Asn Leu Thr Cys Arg Ser Leu
            660                 665                 670
Ser Tyr Pro Asp Glu Glu Cys Asn Glu Ala Cys Leu Glu Gly Cys Phe
            675                 680                 685
Cys Pro Pro Gly Leu Tyr Met Asp Glu Arg Gly Asp Cys Val Pro Lys
    690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
                725                 730                 735
His Cys Thr Met Ser Gly Val Pro Gly Ser Leu Leu Pro Asp Ala Val
            740                 745                 750
Leu Ser Ser Pro Leu Ser His Arg Ser Lys Arg Ser Leu Ser Cys Arg
            755                 760                 765
Pro Pro Met Val Lys Leu Val Cys Pro Ala Asp Asn Leu Arg Ala Glu
    770                 775                 780
Gly Leu Glu Cys Thr Lys Thr Cys Gln Asn Tyr Asp Leu Glu Cys Met
785                 790                 795                 800
Ser Met Gly Cys Val Ser Gly Cys Leu Cys Pro Pro Gly Met Val Arg
            805                 810                 815
His Glu Asn Arg Cys Val Ala Leu Glu Arg Cys Pro Cys Phe His Gln
            820                 825                 830
Gly Lys Glu Tyr Ala Pro Gly Glu Thr Val Lys Ile Gly Cys Asn Thr
            835                 840                 845
Cys Val Cys Arg Asp Arg Lys Trp Asn Cys Thr Asp His Val Cys Asp
    850                 855                 860
Ala Thr Cys Ser Thr Ile Gly Met Ala His Tyr Leu Thr Phe Asp Gly
865                 870                 875                 880
Leu Lys Tyr Leu Phe Pro Gly Glu Cys Gln Tyr Val Leu Val Gln Asp
            885                 890                 895
Tyr Cys Gly Ser Asn Pro Gly Thr Phe Arg Ile Leu Val Gly Asn Lys
            900                 905                 910
Gly Cys Ser His Pro Ser Val Lys Cys Lys Arg Val Thr Ile Leu
            915                 920                 925
Val Glu Gly Gly Glu Ile Glu Leu Phe Asp Gly Glu Val Asn Val Lys
            930                 935                 940
Arg Pro Met Lys Asp Glu Thr His Phe Glu Val Val Glu Ser Gly Arg
945                 950                 955                 960
Tyr Ile Ile Leu Leu Leu Gly Lys Ala Leu Ser Val Val Trp Asp Arg
            965                 970                 975
```

```
His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
        995                 1000                1005

Ser Ser Asn Leu Gln Val Glu Glu Asp Pro Val Asp Phe Gly Asn
    1010                1015                1020

Ser Trp Lys Val Ser Ser Gln Cys Ala Asp Thr Arg Lys Val Pro
    1025                1030                1035

Leu Asp Ser Ser Pro Ala Thr Cys His Asn Asn Ile Met Lys Gln
    1040                1045                1050

Thr Met Val Asp Ser Ser Cys Arg Ile Leu Thr Ser Asp Val Phe
    1055                1060                1065

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
    1085                1090                1095

Cys Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Cys Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro Thr
    1235                1240                1245

Asp Ala Pro Val Ser Pro Thr Thr Leu Tyr Val Glu Asp Ile Ser
    1250                1255                1260

Glu Pro Pro Leu His Asp Phe Tyr Cys Ser Arg Leu Leu Asp Leu
    1265                1270                1275

Val Phe Leu Leu Asp Gly Ser Ser Arg Leu Ser Glu Ala Glu Phe
    1280                1285                1290

Glu Val Leu Lys Ala Phe Val Val Asp Met Met Glu Arg Leu Arg
    1295                1300                1305

Ile Ser Gln Lys Trp Val Arg Val Ala Val Val Glu Tyr His Asp
    1310                1315                1320

Gly Ser His Ala Tyr Ile Gly Leu Lys Asp Arg Lys Arg Pro Ser
    1325                1330                1335

Glu Leu Arg Arg Ile Ala Ser Gln Val Lys Tyr Ala Gly Ser Gln
    1340                1345                1350

Val Ala Ser Thr Ser Glu Val Leu Lys Tyr Thr Leu Phe Gln Ile
    1355                1360                1365

Phe Ser Lys Ile Asp Arg Pro Glu Ala Ser Arg Ile Thr Leu Leu
```

-continued

```
                1370                1375                1380
Leu Met Ala Ser Gln Glu Pro Gln Arg Met Ser Arg Asn Phe Val
    1385                1390                1395
Arg Tyr Val Gln Gly Leu Lys Lys Lys Val Ile Val Ile Pro
    1400                1405                1410
Val Gly Ile Gly Pro His Ala Asn Leu Lys Gln Ile Arg Leu Ile
    1415                1420                1425
Glu Lys Gln Ala Pro Glu Asn Lys Ala Phe Val Leu Ser Ser Val
    1430                1435                1440
Asp Glu Leu Glu Gln Gln Arg Asp Glu Ile Val Ser Tyr Leu Cys
    1445                1450                1455
Asp Leu Ala Pro Glu Ala Pro Pro Pro Thr Leu Pro Pro Asp Met
    1460                1465                1470
Ala Gln Val Thr Val Gly Pro Gly Leu Leu Gly Val Ser Thr Leu
    1475                1480                1485
Gly Pro Lys Arg Asn Ser Met Val Leu Asp Val Ala Phe Val Leu
    1490                1495                1500
Glu Gly Ser Asp Lys Ile Gly Glu Ala Asp Phe Asn Arg Ser Lys
    1505                1510                1515
Glu Phe Met Glu Glu Val Ile Gln Arg Met Asp Val Gly Gln Asp
    1520                1525                1530
Ser Ile His Val Thr Val Leu Gln Tyr Ser Tyr Met Val Thr Val
    1535                1540                1545
Glu Tyr Pro Phe Ser Glu Ala Gln Ser Lys Gly Asp Ile Leu Gln
    1550                1555                1560
Arg Val Arg Glu Ile Arg Tyr Gln Gly Gly Asn Arg Thr Asn Thr
    1565                1570                1575
Gly Leu Ala Leu Arg Tyr Leu Ser Asp His Ser Phe Leu Val Ser
    1580                1585                1590
Gln Gly Asp Arg Glu Gln Ala Pro Asn Leu Val Tyr Met Val Thr
    1595                1600                1605
Gly Asn Pro Ala Ser Asp Glu Ile Lys Arg Leu Pro Gly Asp Ile
    1610                1615                1620
Gln Val Val Pro Ile Gly Val Gly Pro Asn Ala Asn Val Gln Glu
    1625                1630                1635
Leu Glu Arg Ile Gly Trp Pro Asn Ala Pro Ile Leu Ile Gln Asp
    1640                1645                1650
Phe Glu Thr Leu Pro Arg Glu Ala Pro Asp Leu Val Leu Gln Arg
    1655                1660                1665
Cys Cys Ser Gly Glu Gly Leu Gln Ile Pro Thr Leu Ser Pro Ala
    1670                1675                1680
Pro Asp Cys Ser Gln Pro Leu Asp Val Ile Leu Leu Asp Gly
    1685                1690                1695
Ser Ser Ser Phe Pro Ala Ser Tyr Phe Asp Glu Met Lys Ser Phe
    1700                1705                1710
Ala Lys Ala Phe Ile Ser Lys Ala Asn Ile Gly Pro Arg Leu Thr
    1715                1720                1725
Gln Val Ser Val Leu Gln Tyr Gly Ser Ile Thr Thr Ile Asp Val
    1730                1735                1740
Pro Trp Asn Val Val Pro Glu Lys Ala His Leu Leu Ser Leu Val
    1745                1750                1755
Asp Val Met Gln Arg Glu Gly Gly Pro Ser Gln Ile Gly Asp Ala
    1760                1765                1770
```

-continued

Leu Gly Phe Ala Val Arg Tyr Leu Thr Ser Glu Met His Gly Ala
1775                 1780                1785

Arg Pro Gly Ala Ser Lys Ala Val Val Ile Leu Val Thr Asp Val
1790                 1795                1800

Ser Val Asp Ser Val Asp Ala Ala Asp Ala Ala Arg Ser Asn
1805                 1810                1815

Arg Val Thr Val Phe Pro Ile Gly Ile Gly Asp Arg Tyr Asp Ala
1820                 1825                1830

Ala Gln Leu Arg Ile Leu Ala Gly Pro Ala Gly Asp Ser Asn Val
1835                 1840                1845

Val Lys Leu Gln Arg Ile Glu Asp Leu Pro Thr Met Val Thr Leu
1850                 1855                1860

Gly Asn Ser Phe Leu His Lys Leu Cys Ser Gly Phe Val Arg Ile
1865                 1870                1875

Cys Met Asp Glu Asp Gly Asn Glu Lys Arg Pro Gly Asp Val Trp
1880                 1885                1890

Thr Leu Pro Asp Gln Cys His Thr Val Thr Cys Gln Pro Asp Gly
1895                 1900                1905

Gln Thr Leu Leu Lys Ser His Arg Val Asn Cys Asp Arg Gly Leu
1910                 1915                1920

Arg Pro Ser Cys Pro Asn Ser Gln Ser Pro Val Lys Val Glu Glu
1925                 1930                1935

Thr Cys Gly Cys Arg Trp Thr Cys Pro Cys Val Cys Thr Gly Ser
1940                 1945                1950

Ser Thr Arg His Ile Val Thr Phe Asp Gly Gln Asn Phe Lys Leu
1955                 1960                1965

Thr Gly Ser Cys Ser Tyr Val Leu Phe Gln Asn Lys Glu Gln Asp
1970                 1975                1980

Leu Glu Val Ile Leu His Asn Gly Ala Cys Ser Pro Gly Ala Arg
1985                 1990                1995

Gln Gly Cys Met Lys Ser Ile Glu Val Lys His Ser Ala Leu Ser
2000                 2005                2010

Val Glu Leu His Ser Asp Met Glu Val Thr Val Asn Gly Arg Leu
2015                 2020                2025

Val Ser Val Pro Tyr Val Gly Gly Asn Met Glu Val Asn Val Tyr
2030                 2035                2040

Gly Ala Ile Met His Glu Val Arg Phe Asn His Leu Gly His Ile
2045                 2050                2055

Phe Thr Phe Thr Pro Gln Asn Asn Glu Phe Gln Leu Gln Leu Ser
2060                 2065                2070

Pro Lys Thr Phe Ala Ser Lys Thr Tyr Gly Leu Cys Gly Ile Cys
2075                 2080                2085

Asp Glu Asn Gly Ala Asn Asp Phe Met Leu Arg Asp Gly Thr Val
2090                 2095                2100

Thr Thr Asp Trp Lys Thr Leu Val Gln Glu Trp Thr Val Gln Arg
2105                 2110                2115

Pro Gly Gln Thr Cys Gln Pro Ile Leu Glu Glu Gln Cys Leu Val
2120                 2125                2130

Pro Asp Ser Ser His Cys Gln Val Leu Leu Leu Pro Leu Phe Ala
2135                 2140                2145

Glu Cys His Lys Val Leu Ala Pro Ala Thr Phe Tyr Ala Ile Cys
2150                 2155                2160

-continued

```
Gln Gln Asp Ser Cys His Gln Glu Gln Val Cys Glu Val Ile Ala
    2165                2170                2175

Ser Tyr Ala His Leu Cys Arg Thr Asn Gly Val Cys Val Asp Trp
    2180                2185                2190

Arg Thr Pro Asp Phe Cys Ala Met Ser Cys Pro Pro Ser Leu Val
    2195                2200                2205

Tyr Asn His Cys Glu His Gly Cys Pro Arg His Cys Asp Gly Asn
    2210                2215                2220

Val Ser Ser Cys Gly Asp His Pro Ser Glu Gly Cys Phe Cys Pro
    2225                2230                2235

Pro Asp Lys Val Met Leu Glu Gly Ser Cys Val Pro Glu Glu Ala
    2240                2245                2250

Cys Thr Gln Cys Ile Gly Glu Asp Gly Val Gln His Gln Phe Leu
    2255                2260                2265

Glu Ala Trp Val Pro Asp His Gln Pro Cys Gln Ile Cys Thr Cys
    2270                2275                2280

Leu Ser Gly Arg Lys Val Asn Cys Thr Thr Gln Pro Cys Pro Thr
    2285                2290                2295

Ala Lys Ala Pro Thr Cys Gly Leu Cys Glu Val Ala Arg Leu Arg
    2300                2305                2310

Gln Asn Ala Asp Gln Cys Cys Pro Glu Tyr Glu Cys Val Cys Asp
    2315                2320                2325

Pro Val Ser Cys Asp Leu Pro Pro Val Pro His Cys Glu Arg Gly
    2330                2335                2340

Leu Gln Pro Thr Leu Thr Asn Pro Gly Glu Cys Arg Pro Asn Phe
    2345                2350                2355

Thr Cys Ala Cys Arg Lys Glu Glu Cys Lys Arg Val Ser Pro Pro
    2360                2365                2370

Ser Cys Pro Pro His Arg Leu Pro Thr Leu Arg Lys Thr Gln Cys
    2375                2380                2385

Cys Asp Glu Tyr Glu Cys Ala Cys Asn Cys Val Asn Ser Thr Val
    2390                2395                2400

Ser Cys Pro Leu Gly Tyr Leu Ala Ser Thr Ala Thr Asn Asp Cys
    2405                2410                2415

Gly Cys Thr Thr Thr Thr Cys Leu Pro Asp Lys Val Cys Val His
    2420                2425                2430

Arg Ser Thr Ile Tyr Pro Val Gly Gln Phe Trp Glu Glu Gly Cys
    2435                2440                2445

Asp Val Cys Thr Cys Thr Asp Met Glu Asp Ala Val Met Gly Leu
    2450                2455                2460

Arg Val Ala Gln Cys Ser Gln Lys Pro Cys Glu Asp Ser Cys Arg
    2465                2470                2475

Ser Gly Phe Thr Tyr Val Leu His Glu Gly Glu Cys Cys Gly Arg
    2480                2485                2490

Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
```

```
                    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 11
<211> LENGTH: 623
<212> TYPE: PRT
<213> ORGANISM: Homo sapiens

<400> SEQUENCE: 11

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
                20                  25                  30

Thr Thr Ile Leu His Leu Ser Glu Asn Leu Leu Tyr Thr Phe Ser Leu
            35                  40                  45

Ala Thr Leu Met Pro Tyr Thr Arg Leu Thr Gln Leu Asn Leu Asp Arg
        50                  55                  60

Cys Glu Leu Thr Lys Leu Gln Val Asp Gly Thr Leu Pro Val Leu Gly
65                  70                  75                  80

Thr Leu Asp Leu Ser His Asn Gln Leu Gln Ser Leu Pro Leu Leu Gly
                85                  90                  95
```

```
Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Ala Thr Arg Thr Val Val Lys Phe Pro Thr Lys Ala His Thr
    290                 295                 300

Thr Pro Trp Gly Leu Phe Tyr Ser Trp Ser Thr Ala Ser Leu Asp Ser
305                 310                 315                 320

Gln Met Pro Ser Ser Leu His Pro Thr Gln Glu Ser Thr Lys Glu Gln
                325                 330                 335

Thr Thr Phe Pro Pro Arg Trp Thr Pro Asn Phe Thr Leu His Met Glu
            340                 345                 350

Ser Ile Thr Phe Ser Lys Thr Pro Lys Ser Thr Thr Glu Pro Thr Pro
        355                 360                 365

Ser Pro Thr Thr Ser Glu Pro Val Pro Glu Pro Ala Pro Asn Met Thr
    370                 375                 380

Thr Leu Glu Pro Thr Pro Ser Pro Thr Thr Pro Glu Pro Thr Ser Glu
385                 390                 395                 400

Pro Ala Pro Ser Pro Thr Thr Pro Glu Pro Thr Ser Glu Pro Ala Pro
                405                 410                 415

Ser Pro Thr Thr Pro Glu Pro Thr Pro Ile Pro Thr Ile Ala Thr Ser
            420                 425                 430

Pro Thr Ile Leu Val Ser Ala Thr Ser Leu Ile Thr Pro Lys Ser Thr
        435                 440                 445

Phe Leu Thr Thr Thr Lys Pro Val Ser Leu Leu Glu Ser Thr Lys Lys
    450                 455                 460

Thr Ile Pro Glu Leu Asp Gln Pro Pro Lys Leu Arg Gly Val Leu Gln
465                 470                 475                 480

Gly His Leu Glu Ser Ser Arg Asn Asp Pro Phe Leu His Pro Asp Phe
                485                 490                 495

Cys Cys Leu Leu Pro Leu Gly Phe Tyr Val Leu Gly Leu Phe Trp Leu
            500                 505                 510

Leu Phe Ala Ser Val Val Leu Ile Leu Leu Leu Ser Trp Val Gly His
```

```
                515                 520                 525
Val Lys Pro Gln Ala Leu Asp Ser Gly Gln Gly Ala Ala Leu Thr Thr
    530                 535                 540

Ala Thr Gln Thr Thr His Leu Glu Leu Gln Arg Gly Arg Gln Val Thr
545                 550                 555                 560

Val Pro Arg Ala Trp Leu Leu Phe Leu Arg Gly Ser Leu Pro Thr Phe
                565                 570                 575

Arg Ser Ser Leu Phe Leu Trp Val Arg Pro Asn Gly Arg Val Gly Pro
            580                 585                 590

Leu Val Ala Gly Arg Arg Pro Ser Ala Leu Ser Gln Gly Arg Gly Gln
        595                 600                 605

Asp Leu Leu Ser Thr Val Ser Ile Arg Tyr Ser Gly His Ser Leu
    610                 615                 620
```

METHODS AND KITS FOR MEASURING VON WILLEBRAND FACTOR

CROSS-REFERENCE TO RELATED APPLICATIONS

This application is a continuation of U.S. patent application Ser. No. 12/197,057, filed Aug. 22, 2008, now U.S. Pat. No. 8,163,496 which claims the benefit of U.S. Provisional Patent Application No. 60/957,604, filed Aug. 23, 2007, both of which are incorporated herein by reference as if set forth in their entirety for all purposes.

STATEMENT REGARDING FEDERALLY SPONSORED RESEARCH

This invention was made with government support under Grant Numbers RO1-HL033721 and RO1-HL081588 awarded by the National Institutes of Health. The government has certain rights in this invention.

BACKGROUND

The invention relates generally to methods and kits for measuring von Willebrand factor (VWF), and more particularly to methods and kits for measuring VWF that do not require a platelet aggregation agonist, such as ristocetin.

VWF is a multimeric glycoprotein synthesized by megakaryocytes and endothelial cells, which is subsequently secreted into blood plasma as a spectrum of multimers. VWF binds other proteins, especially proteins involved in hemostasis, such as Factor VIII (an essential clotting factor that participates in the intrinsic pathway of blood coagulation) and platelet glycoprotein Ib (GPIb; a component of a platelet adhesion receptor complex). VWF is deficient or defective in von Willebrand disease (VWD) and is involved in a large number of other diseases, including thrombotic thrombocytopenic purpura, Heyde's syndrome and possibly hemolytic-uremic syndrome. See, Sadler J, "Biochemistry and genetics of von Willebrand factor". Annu Rev. Biochem. 67:395-424 (1998). VWF levels can be affected by many factors including ABO blood group and ethnicity.

VWD is a common bleeding disorder characterized by either qualitative or quantitative defects in tests for VWF. Symptoms of VWD include easy bruising, menorrhagia and epistaxis. Currently, many types of hereditary VWD are known (e.g., type 1; type 2A, 2B, 2M, 2N and type 3, as well as platelet-type, pseudo VWD, which results from a defect in platelet GPIb); however, acquired forms of VWD are also known, but are less frequently observed. Of particular interest herein is platelet-type, pseudo VWD. In contrast to the other forms of VWD, the genetic defect in platelet-type, pseudo VWD is in platelets rather than VWF and is characterized by abnormally high binding affinity of an individual's platelets to VWF, leading to a characteristic platelet hyper-responsiveness in vitro to a low concentration of ristocetin.

Additional screening tests for VWD include those that measure Factor VIII activity, VWF antigen (VWF:Ag), VWF binding to collagen (VWF:CB) and VWF ristocetin cofactor activity (VWF:RCo). Of particular interest herein is VWF:RCo, which is presently the standard for measurement of VWF function. VWF:RCo utilizes an ability of VWF to bind platelet GPIb following activation by ristocetin, which results in a VWF-dependent agglutination of platelets that can be measured quantitatively by platelet aggregometry or turbidometry. See, Macfarlane D, et al., "A method for assaying von Willebrand factor (ristocetin cofactor)," Thromb. Diath. Haemorrh. 34:306-308 (1975). In fact, an international reference standard for VWF:RCo was assigned a biologic activity in international units by the World Health Organization (WHO) and the Scientific and Standardization Committee of the International Society on Thrombosis and Haemostasis (ISTH).

Unfortunately, VWF:RCo, has several shortcomings. For one, VWF:RCo has high intra- and inter-assay imprecision because of its dependence on ristocetin. See, e.g., Chng W, et al., "Differential effect of the ABO blood group on von Willebrand factor collagen binding activity and ristocetin cofactor assay," Blood Coagul. Fibrinolysis 16:75-78 (2005); Favaloro E, "An update on the von Willebrand factor collagen binding assay: 21 years of age and beyond adolescence but not yet a mature adult," Semin. Thromb. Hemost. 33:727-744 (2007); and Riddel A, et al., "Use of the collagen-binding assay for von Willebrand factor in the analysis of type 2M von Willebrand disease: a comparison with the ristocetin cofactor assay," Br. J. Haematol. 116:187-192 (2002). Federici et at recently described an alternative assay with improved reproducibility that used recombinant GPIb in an enzyme-linked immunosorbant assay of VWF binding; however, it is ristocetin dependent. See, Federici A, et al., "A sensitive ristocetin co-factor activity assay with recombinant glycoprotein Ib for diagnosis of patients with low von Willebrand factor levels," Haematologica 89:77-85 (2004).

In addition, VWF:RCo does not always reflect the true in vivo function of VWF when mutations or polymorphisms are in the ristocetin-binding region of VWF. For example, some individuals have VWF mutations that show a reduced interaction with ristocetin such that VWF:RCo is markedly reduced (e.g., <0.12 IU/dL), although they have no bleeding symptoms even with a major surgical challenge. See, Flood V, et al., "Common VWF haplotypes in normal African-Americans and Caucasians recruited into the ZPMCB-VWD and their impact on VWF laboratory testing," Blood 10:Abstract 714 (2007); Mackie, et al., "Ristocetin-induced platelet agglutination in Afro-Caribbean and Caucasian people," Br. J. Haematol. 50:171-173 (1982); and Miller C, et al., "Measurement of von Willebrand factor activity: relative effects of ABO blood type and race," J. Thromb. Haemost. 1:2191-2197 (2003). These individuals, who appear to have a polymorphism in the ristocetin-binding region, do not have an abnormality in the binding of VWF to platelet GPIb.

Furthermore, VWF:RCo is affected by high-affinity VWF/platelet disorders. For example, individuals with platelet-type, pseudo VWD have GPIb mutations that cause spontaneous binding of their platelets to VWF. See, Franchini M, et al., "Clinical, laboratory and therapeutic aspects of platelet-type von Willebrand disease," Int. J. Lab. Hematol. 30:91-94 (2008); Miller J & Castella A, "Platelet-type von Willebrand's disease: characterization of a new bleeding disorder," Blood 60:790-794 (1982); and Miller J, "Platelet-type von Willebrand's Disease," Thromb. Haemost. 75:865-869 (1996). Likewise, individuals with type 2B VWD have VWF mutations that cause spontaneous binding to platelets. See, Weiss H, "Type 2B von Willebrand disease and related disorders of patients with increased ristocetin-induced platelet aggregation: what they tell us about the role of von Willebrand factor in hemostasis," J. Thromb. Haemost. 2:2055-2056 (2004).

Because of the wide variability and reproducibility of VWF:RCo, the art desires a VWF function assay that does not require a platelet aggregation agonist, such as ristocetin (i.e., ristocetinless).

BRIEF SUMMARY

The invention relates generally to methods and kits for measuring VWF without requiring a platelet agglutination agonist by utilizing recombinant platelet GPIb gain-of-function mutations. As used herein, a "platelet agglutination agonist" means an agent that facilitates adhesion between VWF and GPIb in platelet agglutination tests. Examples of platelet agglutination agonist include, but are not limited to, ristocetin and botrocetin.

In a first aspect, the present invention is summarized as a method of measuring VWF without requiring a platelet agglutination agonist by providing a surface with immobilized recombinant platelet GPIbα having at least two mutations selected from G233V, D235Y and M239V relative to SEQ ID NO:11 or a functional fragment thereof. The method also includes contacting a sample having or suspected of having VWF with the immobilized GPIbα or functional fragment thereof without using the platelet agglutination agonist. The method also includes detecting a complex, if any, of VWF and the immobilized GPIbα or functional fragment thereof.

In some embodiments of the first aspect, the surface can be a cell surface such that the method is a flow cytometry (FC) or fluorescence-activated cell sorting (FACS) assay. Suitable host cells can be a *Xenopus* oocyte, CHO-K1 cell, L929 cell, HEK-293T cell, COS-7 cell or S2 cell engineered to comprise a polynucleotide encoding platelet GPIbα having the at least two mutations selected from the group consisting of G233V, D235Y and M239V relative to SEQ ID NO:11 or a functional fragment thereof. The host cell also can be engineered to further comprise a polynucleotide encoding platelet glycoprotein Ibβ (GPIbβ; SEQ ID NO:4) and/or optionally platelet glycoprotein IX (GP-IX; SEQ ID NO:8) or functional fragments thereof.

In some embodiments of the first aspect, the surface can be a solid-phase surface such that the method is an enzyme-linked immunosorbant assay (ELISA). The solid-phase surface can be agarose, glass, latex or plastic.

In some embodiments of the first aspect, the complex can be detected with a labeled anti-VWF antibody or functional fragment thereof, such as a fluorescently labeled antibody or fluorescently labeled functional fragment thereof. Alternatively, the complex can be detected by surface plasmon resonance or quasi-elastic light scattering.

In some embodiments of the first aspect, the sample can be a biological sample from an individual having or suspected of having VWD, such as plasma.

In some embodiments of the first aspect, the at least two mutations can be D235Y/G233V, D235Y/M239V or G233V/M239V. In other embodiments of the first aspect, the at least two mutation can be a triple mutation, such as D235Y/G233V/M239V.

In a second aspect, the present invention is summarized as a kit for measuring VWF that includes recombinant platelet GPIbα having at least two mutations selected from G233V, D235Y and M239V relative to SEQ ID NO:11 or a functional fragment thereof. The kit also includes a reagent to detect a complex of VWF and GPIbα.

In some embodiments of the second aspect, the reagent can be a labeled anti-VWF antibody or labeled functional fragment thereof, such as a fluorescently labeled antibody or fluorescently labeled functional fragment thereof.

In some embodiments of the second aspect, the kit further includes a negative or positive control or both. If included, the negative control can be VWF-depleted plasma. If included, the positive control can be pooled plasma from individuals that do not have VWD or can be a commercially available standard, such as those available from WHO and ISTH. In other embodiments of the second aspect, the kit further includes an abnormal control. If included, the abnormal control can be pooled plasma from individuals with variant forms of VWD, such as type-2A, 2B or 2M VWD, as well as pooled plasma from individuals with true loss of in vivo VWF function or pooled plasma individuals that are not appropriately assayed using VWF:RCo (i.e., plasma from individuals having any gain-of-function mutation in VWF).

In some embodiments of the second aspect, the at least two mutations can be selected from D235Y/G233V, D235Y/M239V or G233V/M239V. In other embodiments of the second aspect, the at least two mutations can be a triple mutation, such as D235Y/G233V/M239V.

In some embodiments of the second aspect, the recombinant platelet GPIbα having at least two mutations selected from G233V, D235Y and M239V relative to SEQ ID NO:11 or functional fragment thereof can be immobilized to a surface. In certain embodiments, the surface can be a host cell surface of a host cell that does not natively express platelet GPIbα, as described above. In certain other embodiments, the surface can be a solid-phase surface, as described above.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 2A, y-axis is mean fluorescence and x-axis is log ristocetin concentration in mg/ml), ristocetin (FIG. 2B, y-axis is mean fluorescence and x-axis is log ristocetin concentration in mg/ml) and botrocetin (FIG. 2C, y-axis is mean fluorescence and x-axis is log botrocetin concentration in mg/ml) during FACS. Mock is a HEK-293T cells transfected with an empty expression vector.

Figure 1:
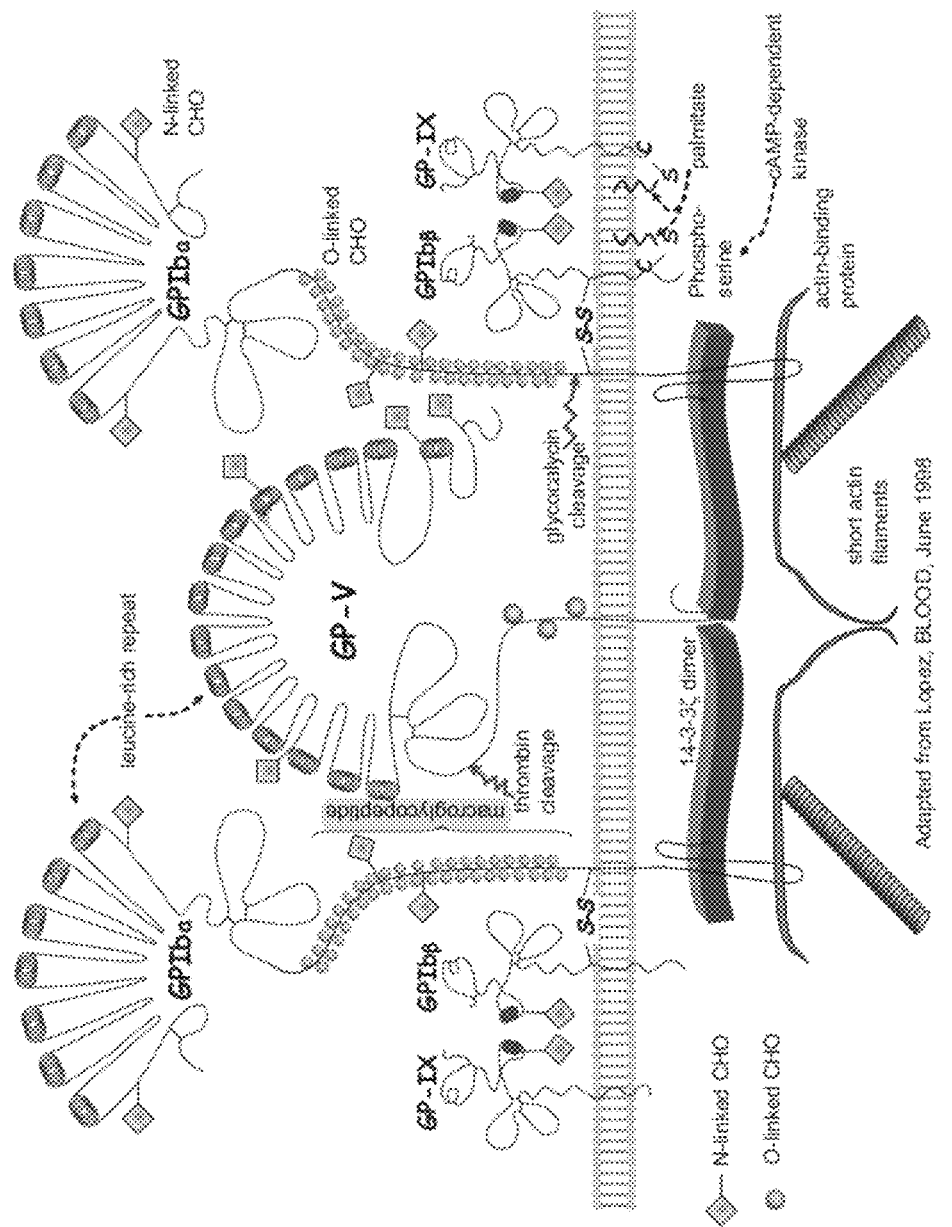
FIG. 1 is a schematic illustration of the platelet adhesion receptor, which shows the components of the receptor, including GPIbα, GPIbIβ, GP-V and GP-IX.

While the present invention is susceptible to various modifications and alternative forms, exemplary embodiments thereof are shown by way of example in the drawings and are herein described in detail. It should be understood, however, that the description of preferred embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF PREFERRED EMBODIMENTS

The present invention stems from the inventor's observation that some individuals with VWD have VWF mutations that lower VWF:RCo (i.e., <10 IU/dL), even though their in vivo VWF function is normal (i.e., VWF still binds to the platelet adhesion receptor component GPIb). See, Friedman K, et al., "Factitious diagnosis of type 2M von Willebrand disease (VWD) with a mutation in von Willebrand factor (VWF) that affects the ristocetin cofactor assay but does not significantly affect VWF function in vitro," Blood 98:536a (2001).

In contrast, other individuals with VWD (i.e., type 2B and platelet-type VWD) have VWF or GPIbα mutations that lower the concentration of ristocetin required for platelet aggregation in an assay for VWF function. This paradox results from gain-of-function mutations that cause VWF multimers and the GPIb receptors on platelets to bind more tightly to one another. The inventor hypothesized that recombinant gain-of-function GPIbα mutations could be useful in assays for VWF function, thereby avoiding ristocetin (i.e., ristocetinless). As used herein, "ristocetinless" or "agonistless" means that ristocetin or other platelet agglutination agonists (i.e., botrocetin) are not required in a VWF assay.

The present invention therefore broadly relates to novel methods and kits for VWF utilizing gain-of-function GPIbα mutations, especially GPIbα mutations identified in individuals having platelet-type, pseudo VWD, to measure VWF (herein called "VWF:IbCo"). The methods and kits are useful in a variety of applications. For example, the methods and kits disclosed herein may be used for diagnosing VWD in an individual suspected of having VWD, classifying VWD in an individual diagnosed with VWD and monitoring treatment in an individual having VWD.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

As used herein, "about" means within 5% of a stated concentration range, purity range, temperature range or stated time frame.

As used herein, a "coding sequence" means a sequence that encodes a particular polypeptide, such as GPIbα, and is a nucleic acid sequence that is transcribed (in the case of DNA) and translated (in the case of mRNA) into that polypeptide in vitro or in vivo when placed under the control of appropriate regulatory sequences. The boundaries of the coding sequence are determined by a start codon at a 5' (amino) terminus and a translation stop codon at a 3' (carboxy) terminus. A coding sequence can include, but is not limited to, viral nucleic acid sequences, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

As used herein, an "expression sequence" means a control sequence operably linked to a coding sequence.

As used herein, "control sequences" means promoter sequences, polyadenylation signals, transcription termination sequences, upstream regulatory domains, origins of replication, internal ribosome entry sites ("IRES"), enhancers, and the like, which collectively provide for replication, transcription and translation of a coding sequence in a recipient cell. Not all of these control sequences need always be present so long as the selected coding sequence is capable of being replicated, transcribed and translated in an appropriate host cell.

As used herein, a "promoter" means a nucleotide region comprising a nucleic acid (i.e., DNA) regulatory sequence, wherein the regulatory sequence is derived from a gene that is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is repressed by an analyte, cofactor, regulatory protein, etc.) and "constitutive promoters" (where expression of a polynucleotide sequence operably linked to the promoter is unregulated and therefore continuous).

As used herein, a "nucleic acid" sequence means a DNA or RNA sequence. The term encompasses sequences that include, but are not limited to, any of the known base analogues of DNA and RNA such as 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine and 2,6-diaminopurine.

As used herein, "operably linked" means that elements of an expression sequence are configured so as to perform their usual function. Thus, control sequences (i.e., promoters) operably linked to a coding sequence are capable of effecting expression of the coding sequence. The control sequences need not be contiguous with the coding sequence, so long as they function to direct the expression thereof. For example, intervening untranslated, yet transcribed, sequences can be present between a promoter and a coding sequence, and the promoter sequence can still be considered "operably linked" to the coding sequence.

As used herein, "operable interaction" means that subunits of a polypeptide (e.g., the components of the platelet adhesion receptor, such as GPIbβ and/or GP-IX), and any other accessory proteins, that are heterologously expressed in a host cell assemble into a functioning platelet adhesion receptor (i.e., capable of binding with VWF or functional fragments thereof capable of binding VWF).

As used herein, a "vector" means a replicon, such as a plasmid, phage or cosmid, to which another nucleic acid segment may be attached so as to bring about the replication of the attached segment. A vector is capable of transferring gene sequences to target cells (e.g., bacterial plasmid vectors, particulate carriers and liposomes).

Typically, the terms "vector construct," "expression vector," "gene expression vector," "gene delivery vector," "gene transfer vector" and "expression cassette" all refer to an assembly that is capable of directing the expression of a coding sequence or gene of interest. Thus, the terms include cloning and expression vehicles.

As used herein, an "isolated polynucleotide" or "isolated polypeptide" means a polynucleotide or polypeptide isolated from its natural environment or prepared using synthetic methods such as those known to one of ordinary skill in the art. Complete purification is not required in either case. The polynucleotides and polypeptides described herein can be isolated and purified from normally associated material in conventional ways, such that in the purified preparation the polynucleotide or polypeptide is the predominant species in the preparation. At the very least, the degree of purification is such that extraneous material in the preparation does not interfere with use of the polynucleotide or polypeptide in the manner disclosed herein. The polynucleotide or polypeptide is at least about 85% pure; alternatively, at least about 95% pure; and alternatively, at least about 99% pure.

Further, an isolated polynucleotide has a structure that is not identical to that of any naturally occurring nucleic acid molecule or to that of any fragment of a naturally occurring genomic nucleic acid spanning more than one gene. An isolated polynucleotide also includes, without limitation, (a) a nucleic acid having a sequence of a naturally occurring genomic or extrachromosomal nucleic acid molecule, but which is not flanked by the coding sequences that flank the sequence in its natural position; (b) a nucleic acid incorporated into a vector or into a prokaryote or eukaryote host cell's genome such that the resulting polynucleotide is not identical to any naturally occurring vector or genomic DNA; (c) a separate molecule such as a cDNA, a genomic fragment, a fragment produced by polymerase chain reaction (PCR) or a restriction fragment; and (d) a recombinant nucleotide sequence that is part of a hybrid gene (i.e., a gene encoding a fusion protein). Specifically excluded from this definition are nucleic acids present in mixtures of clones, e.g., as these occur in a DNA library such as a cDNA or genomic DNA library. An isolated polynucleotide can be modified or unmodified DNA or RNA, whether fully or partially single-stranded or double-stranded or even triple-stranded. In addition, an isolated polynucleotide can be chemically or enzymatically modified and can include so-called non-standard bases such as inosine.

As used herein, "homologous" means those polynucleotides or polypeptides sharing at least about 90% or at least about 95% sequence identity to, e.g., SEQ ID NOS:1-6 & 11, that result in functional polypeptides that bind VWF. For example, a polypeptide that is at least about 90% or at least about 95% identical to the GPIbα mutations discussed herein is expected to be a constituent of the platelet adhesion receptor. One of ordinary skill in the art understands that modifications to either the polynucleotide or the polypeptide includes substitutions, insertions (e.g., adding no more than about ten nucleotides or amino acids) and deletions (e.g., deleting no more than about ten nucleotides or amino acids).

These modifications can be introduced into the polynucleotide or polypeptide described below without abolishing structure and ultimately, function. Polynucleotides and/or polypeptides containing such modifications can be used in the methods of the present invention. Such polypeptides can be identified by using the screening methods described below.

An isolated nucleic acid containing a polynucleotide (or its complement) that can hybridize to any of the uninterrupted nucleic acid sequences described above, under either stringent or moderately stringent hybridization conditions, is also within the scope of the present invention. Stringent hybridization conditions are defined as hybridizing at 68° C. in 5×SSC/5×Denhardt's solution/1.0% SDS, and washing in 0.2×SSC/0.1% SDS+/−100 µg/ml denatured salmon sperm DNA at room temperature, and moderately stringent hybridization conditions are defined as washing in the same buffer at 42° C. Additional guidance regarding such conditions is readily available in the art, e.g., in Sambrook J, et al. (eds.), "Molecular cloning: a laboratory manual," (3rd ed. Cold Spring Harbor Press, Cold Spring Harbor, N.Y. 2001); and Ausubel F, et al. (eds.), "Current Protocols in Molecular Biology," (John Wiley & Sons, N.Y. 1995), each of which is incorporated herein by reference as if set forth in its entirety.

It is well known in the art that amino acids within the same conservative group can typically substitute for one another without substantially affecting the function of a protein. For the purpose of the present invention, such conservative groups are set forth in Table 1 and are based on shared properties.

TABLE 1

Amino Acid Conservative Substitutions.

| Original Residue | Conservative Substitution |
| --- | --- |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

As used herein, an "antibody" means a monoclonal and polyclonal antibody and can belong to any antibody class (i.e., IgG, IgM, IgA, etc.). One of ordinary skill in the art is familiar with methods for making monoclonal antibodies (Mab). For example, one of ordinary skill in the art can make monoclonal antibodies by isolating lymphocytes and fusing them with myeloma cells, thereby producing hybridomas. See, e.g., Milstein C, "Handbook of experimental immunology," (Blackwell Scientific Pub., 1986); and Goding J, "Monoclonal antibodies: principles and practice," (Academic Press, 1983), each of which is incorporated herein by reference as if set forth in its entirety. The cloned hybridomas are then screened for production of, e.g., "anti-GPIbα" (i.e., antibodies that bind preferentially to GPIbα or fragments thereof) or "anti-VWF" antibodies (i.e., antibodies that bind preferentially to VWF or fragments thereof). Monoclonal antibodies are thus not limited by the manner in which the antibodies are produced, whether such production is in situ or not. Alternatively, antibodies can be produced by recombinant DNA technology including, but not limited, to expression in bacteria, yeast, insect cell lines or mammalian cell lines.

Likewise, one of ordinary skill in the art is familiar with methods of making polyclonal antibodies. For example, one of ordinary skill in the art can make polyclonal antibodies by immunizing a suitable host animal, e.g., such as a rabbit, with an immunogen and using properly diluted serum or isolating immunoglobulins from the serum. The animal may therefore be inoculated with the immunogen, with blood subsequently being removed from the animal and an IgG fraction purified. Other suitable host animals include a chicken, goat, sheep, guinea pig, rat or mouse. If desired, the immunogen may be administered as a conjugate in which the immunogen is coupled, e.g., via a side chain of one of its amino acid residues, to a suitable carrier. The carrier molecule is typically a physiologically acceptable carrier. The antibody obtained may be purified to a purity of up to about 70%, up to about 80%, up to about 90%, up to about 95%, up to about 99% or up to about 100%.

Antibody also encompasses functional fragments, like Fab and F(ab') 2, of anti-GPIbα or anti-VWF antibodies. Treatment of antibodies with proteolytic enzymes, such as papain and pepsin, generates these antibody fragments, especially anti-GPIbα fragments.

Antibodies are typically conjugated to a detectable label for easy visualization. Examples of suitable labels for the methods and kits described herein include, but are not limited to, radiolabels, biotin (which may be detected by avidin or streptavidin conjugated to peroxidase), lanthanides, alkaline phosphatase and fluorescent labels (e.g., fluorescein, rhodamine, especially the Alexa Fluor® family of fluorescent dyes available from Invitrogen/Molecular Probes). Labelling of the antibody can be carried out by, e.g. labeling free amine groups (covalently or non-covalently). Some labels can be detected by using a labeled counter suitable for the detection of the label in question.

Commercially available anti-GPIbα antibodies and anti-VWF antibodies are suitable for use with the methods and kits described herein, and can be obtained from Blood Research Institute (Milwaukee, Wis.) and Dako (Carpinteria, Calif.), respectively.

As shown in FIG. 1, the platelet adhesion receptor is comprised of a combination of four proteins, including GPIb, which is a heterodimer of an alpha chain (GPIbα; GenBank Accession No. NM_000173.4; SEQ ID NOS:1-2 & 11) and a beta chain (GPIbβ; GenBank Accession No. NM_000407.4; SEQ ID NOS:3-4) linked by disulfide bonds. Other components of the receptor include GP-V (GenBank Accession No. NM_004488.2; SEQ ID NOS:5-6) and GP-IX (GenBank Accession No. NM_000174.2; SEQ ID NOS: 7-8). The platelet adhesion receptor binds to VWF (GenBank Accession No. NM_000552.3; SEQ ID NOS:9-10) to regulate hemostasis and thrombosis.

Of particular interest herein is human GPIbα modified so that a platelet aggregation agonist is not required in assays of VWF function. For example, GPIbα can be modified to include the gain-of-function mutations that cause platelet-type, pseudo VWD including, but not limited to, G233V (see, Miller J, et al., "Mutation in the gene encoding the alpha chain of platelet glycoprotein Ib in platelet-type von Willebrand disease," Proc. Natl. Acad. Sci. USA 88:4761-4765 (1991), incorporated herein by reference as if set forth in its entirety); D235V (see, Dong J, et al., "Novel gain-of-function mutations of platelet glycoprotein IBα by valine mutagenesis in the Cys209-Cys248 disulfide loop, which interacts with the A1 domain of VWF. Functional analysis under static and dynamic conditions," J. Biol. Chem. 275:27663-27670 (2000), incorporated herein by reference as if set forth in its entirety); M239V (see, Russell S & Roth G, "Pseudo-von Willebrand disease: a mutation in the platelet glycoprotein Ib alpha gene associated with a hyperactive surface receptor," Blood 81:1787-1791 (1993), incorporated herein by reference as if set forth in its entirety); G233S (Matsubara Y, et al., "Identification of a novel point mutation in platelet glycoprotein Ib, Gly to Ser at residue 233, in a Japanese family with platelet-type von Willebrand disease," J. Thromb. Haemost. 1:2198-2205 (2003)); and K237V (see, Dong et al., supra). Advantageously, the mutation(s) can be in the $Cys^{209}$-$Cys^{248}$ disulfide loop of GPIbα that compromise hemostasis by increasing the affinity of GPIb for VWF. For example, and as shown below, the inventor found that D235Y is another gain-of-function mutation suitable for use with the methods and kits described herein.

As used herein, a "functional fragment" means a fragment of a component of a platelet adhesion receptor, such as a fragment of GPIbα, having at least two of the previously mentioned mutation, yet retaining its ability to interact with VWF or other substrates. For example, the amino terminus of GPIbα retains its ability to interact with VWF. As shown below, fragments of GPIbα as small as 290 amino acids and having two mutations retained an ability to interact with VWF, although smaller fragments are contemplated. With respect to VWF, a functional fragment may comprise at least the A1 domain, which is the GPIb binding domain. With respect to antibodies, functional fragments are those portions of an antibody that bind to a particular epitope, such as the domains indicated above.

As used herein, a "sample" means a biological sample, such as amniotic fluid, aqueous humor, cerebrospinal fluid, interstitial fluid, lymph, plasma, pleural fluid, saliva, serum, sputum, synovial fluid, sweat, tears, urine, breast milk or tissue that has or is suspected of having VWF. With respect to measuring VWF, plasma is a suitable sample.

As used herein, a "surface" means, e.g., a cell surface or solid-phase surface, such as an unsoluble polymer material, which can be an organic polymer, such as polyamide or a vinyl polymer (e.g., poly (meth)acrylate, polystyrene and polyvinyl alcohol or derivates thereof), a natural polymer, such as cellulose, dextrane, agarose, chitin and polyamino acids, or an inorganic polymer, such as glass or plastic. The solid-phase surface can be in the form of a bead, microcarrier, particle, membrane, strip, paper, film, pearl or plate, particularly a microtiter plate.

One aspect of the present invention includes a diagnostic assay for measuring VWF. The underlying methodology of the assay can be FC, FACS or ELISA, each of which is well known to one of ordinary skill in the art. See, e.g., Alice Giva, "Flow cytometry: first principles," (2nd ed. Wiley-Liss, New York, 2001); Howard Shapiro, "Practical flow cytometry," (4th Ed. Wiley-Liss, New York, 2003); Larry Sklar, "Flow cytometry for biotechnology," (Oxford University Press, New York, 2005); J. Paul Robinson, et al., "Handbook of flow cytometry," (Wiley-Liss, New York, 1993); "Flow cytometry in clinical diagnosis," (3rd ed., Carey, McCoy and Keren, eds., ASCP Press 2001); Lequin R, "Enzyme immunoassay (EIA)/enzyme-linked immunosorbent assay (ELISA)," Clin. Chem. 51:2415-2418 (2005); Wide L & Porath J, "Radioimmunoassay of proteins with the use of Sephadex-coupled antibodies," Biochem. Biophys. Acta. 30:257-260 (1966); Engvall E & Perlman P, "Enzyme-linked immunosorbent assay (ELISA). Quantitative assay of immunoglobulin G," Immunochemistry 8:871-874 (1971); and Van Weemen B & Schuurs A, "Immunoassay using antigen-enzyme conjugates," FEBS Letters 15:232-236 (1971), each of which is incorporated herein by reference as if set forth in its entirety.

As noted above, the surface for the methods and kits described herein can be a host cell surface expressing at least platelet GPIbα for use in FACS. For example, one can heterologously express (either transiently or stably) mutant GPIbα or other components of platelet adhesion receptor (i.e., GPIbβ and/or GP-IX) in host cells. Methods of expressing polynucleotides and their encoded platelet glycoprotein receptor polypeptides in heterologous host cells are known to one of ordinary skill in the art. See, e.g., Tait A, et al., "Phenotype changes resulting in high-affinity binding of von Willebrand factor to recombinant glycoprotein Ib-IX: analysis of the platelet-type von Willebrand disease mutations," Blood 98:1812-1818 (2001), incorporated herein by reference as if set forth in its entirety; and Dong et al., supra.

Cells suitable for use herein preferably do not natively display GPIbα or the other components of the platelet adhesion receptor complex. One such cell type is HEK-293T cells (American Type Culture Collection (ATCC); Manassas, Va.; Catalog No. CRL-11268). See also, Graham F, et al., "Characteristics of a human cell line transformed by DNA from human adenovirus type 5," J. Gen. Virol. 36:59-74 (1977), incorporated herein by reference as if set forth in its entirety. HEK-293 cells are easy to reproduce and to maintain, are amenable to transfection using a wide variety of methods, have a high efficiency of transfection and protein production, have faithful translation and processing of proteins and have a small cell size with minimal processes appropriate for electrophysiological experiments.

Another suitable cell type is COS-7 cells (ATCC; Catalog No. CRL-1651). See also, Gluzman Y, "SV40-transformed simian cells support the replication of early SV40 mutants," Cell 23:175-182 (1981), incorporated herein by reference as if set forth in its entirety. Like HEK-293 cells, COS-7 cells are easy to reproduce and maintain and are amenable to transfection using a wide variety of methods.

Yet another suitable cell type is *Xenopus* oocytes. *Xenopus* oocytes are commonly used for heterologous gene expression because of their large size (~1.0 mm), which makes their handling and manipulation easy. *Xenopus* oocytes are readily amenable to injection, and thus express functional proteins when injected with cRNA for an desired protein.

Yet another suitable cell type is S2 *Drosophila melanogaster* cells. S2 cells are ideal for difficult-to-express proteins, and a S2 expression system is commercially available from Invitrogen (Carlsbad, Calif.). The S2 expression system can be engineered to preferably lack the Bip secretion sequence so that the encoded proteins are expressed on the cell surface. Expression of platelet adhesion receptor components in S2 cells was previously shown by Celikel et al. See, Celikel R, et al., "Modulation of alpha-thrombin function by distinct interactions with platelet glycoprotein Ibα," Science 301:218-221 (2003), incorporated herein by reference as if set forth in its entirety.

Any of the contemplated polynucleotides for the platelet adhesion receptor can be cloned into an expression vector (or plurality of expression vectors) engineered to support expression from the polynucleotides. Suitable expression vectors comprise a transcriptional promoter active in a recipient host cell upstream of, e.g., a GPIbα polynucleotide engineered to have the previously mentioned mutations or additional polynucleotides and can optionally comprise a polyA-addition sequence downstream of the polynucleotide.

The vector(s) can be introduced (or co-introduced) by, for example, transfection or lipofection, into recipient host cells competent to receive and express mutant GPIbα and optionally other components of the platelet adhesion receptor. A commercially available lipofection kit, such as a kit available from Mims Corporation (Madison, Wis.) can be employed. Preferably, the recipient host cells do not natively contain GPIbα, so that the presence of it is completely attributable to expression from the introduced expression vector. Suitable recipient host cells are described above and can express the polypeptides on their surface or secrete them.

Alternatively, the surface for the methods and kits described herein can be a solid-phase surface having platelet GPIbα immobilized thereupon by, e.g., covalent attachment or antibodies. Suitable solid-phase surfaces include the solid-phase surfaces described above. One of ordinary skill in the art is familiar with methods for attaching anti-GPIbα antibodies or functional fragments thereof to solid-phase surfaces. For example, the antibody or functional fragment thereof can be immobilized on the surface directly by covalent coupling or via a carrier such as a linker molecule or an antibody immobilized on the solid-phase surface. The antibody can be a polyclonal or monoclonal antibody, such as anti-GPIbα or a functional fragment thereof. Alternatively, the antibody can be an anti-epitope antibody that recognizes an epitope-tag (e.g., biotin, digoxigenin, GST, hexahistidine, hemagglutinin. FLAG™, c-Myc, VSV-G, V5 and HSV) complexed with GPIbα. Commercially available epitope tags and their respective antibodies are suitable for use with the methods and kits described herein, and can be obtained from Sigma Aldrich (St. Louis, Mo.) and Abcam, Inc. (Cambridge, Mass.).

The methods and kits described herein are thus sensitive to the measurement of the more functional, large VWF multimers, correlates with VWF:Ag in individuals with reduced VWF function, and remains unaffected by mutations that affect VWF binding of ristocetin but do not have a bleeding phenotype.

The invention will be more fully understood upon consideration of the following non-limiting Examples.

EXAMPLES

Example 1

Cells Heterologously Expressing Mutant GPIbα Spontaneous Binding in the Absence Ristocetin Methods: A heterologous platelet adhesion receptor expression system was constructed by transiently transfecting HEK-293T cells (ATCC) with a full-length GPIbαconstruct encoding a single mutation (i.e., G233V, D235Y or M239V), a double mutation (i.e., G233V/M239V, G233V/D235Y or D235Y/M239V) a triple mutation (i.e., G233V/D235Y/M239V) relative to SEQ ID NO:11 or wild-type GPIbα (SEQ ID NO:11). Some HEK-293T cells also were transiently transfected with GPIbβ and GP-IX constructs encoding SEQ ID NOS:4 and 8, respectively. A mock group of HEK-293T cells were treated similarly, but were transfected with an expression vector lacking the above constructs, thereby serving as controls.

The constructs were cloned in to a pCI-neo vector (Promega; Madison, Wis.) and expressed in HEK-293T cells as described below. In some instances, separate constructs were made for each GPIbα mutation; however, in other instances, a single construct was made having multiple GPIbα mutations.

Briefly, HEK-293T cells were first seeded until they were 50-80% confluent (i.e., 3.5–4×10$^6$/100 mm dish). Typically, the cells were seeded the day before transfection.

For transfection, Hanks Balanced Salt Solution (HBSS) and OptiMEM (Invitrogen) were warmed to 37° C. 800 µl of OptiMEM was added to 17×100 polystyrene tubes (2 tubes/plate to be transfected). The following was added to one set of tubes: 4.5 µg of DNA (1.5 µg of each construct) and 20 µl PLUS Reagent (Invitrogen). The following was added to another set of tubes: 30 µl Lipofectamine (Invitrogen). Each set was allowed to incubate at room temperature for 15 minutes. The DNA mixture was then added to the Lipofectamine mixture and incubated at room temperature for 15 minutes. During incubation, the cells were washed twice with 5 ml HBSS. 3.4 ml of OptiMEM was added to the DNA/Lipofectamine mixture, and then added to the HEK-293T cells (total volume=5 ml). The cells were then incubated at 37° C. with 5% $CO_2$ for 3-3.5 hours.

Following transfection, the transfection medium was removed and 8 ml of fresh complete medium was added to the cells. The cells were then incubated at 37° C. with 5% $CO_2$ for about 60 hours. Cells were then harvested for use in a standard FACS assay using ristocetin.

For FACS, about 50 µl of a 1:10 dilution of platelet poor plasma (PPP; source of VWF) in assay buffer was added to the plate and serially diluted 1:2 to final dilution of 1:80. ISTH Lot #3 (GTI; Milwaukee, Wis.) was used as a standard and diluted 1:10 in assay buffer and serially diluted 1:2 to a final dilution of 1:320. The plate was then incubated for one hour at room temperature. After the one-hour incubation, the plate was centrifuged again at 1200 rpm for 5 minutes and the supernatant was discarded.

In some experiments, the PPP was diluted in PBS containing 1% BSA and either 1 mg/ml Ristocetin A (American Biochemical & Pharmaceuticals, Ltd.; Marlton, N.J.) or 1 mg/ml Botrocetin (Sigma Aldrich).

Fluorescently labeled antibodies (anti-GPIbα; Blood Research Institute) were diluted to a final concentration of 5 µg/ml in assay buffer. Fluorescently labeled anti-VWF polyclonal was also was diluted to a final concentration of 5 µg/ml in assay buffer and added to transfected cells incubated in PPP. Normal rabbit IgG (NRIgG; Pierce) and AP-1 were added at a concentration of 5 µg/ml to transfected cells as negative and positive controls, respectively. The plate was then incubated in the dark for one hour at room temperature. Assay buffer was added to each well to bring the final volume to 150 µl, and FACS was performed using a BD LSRII System (Becton Dickinson). Results are shown in VWF:IbCo units.

Figure 2:
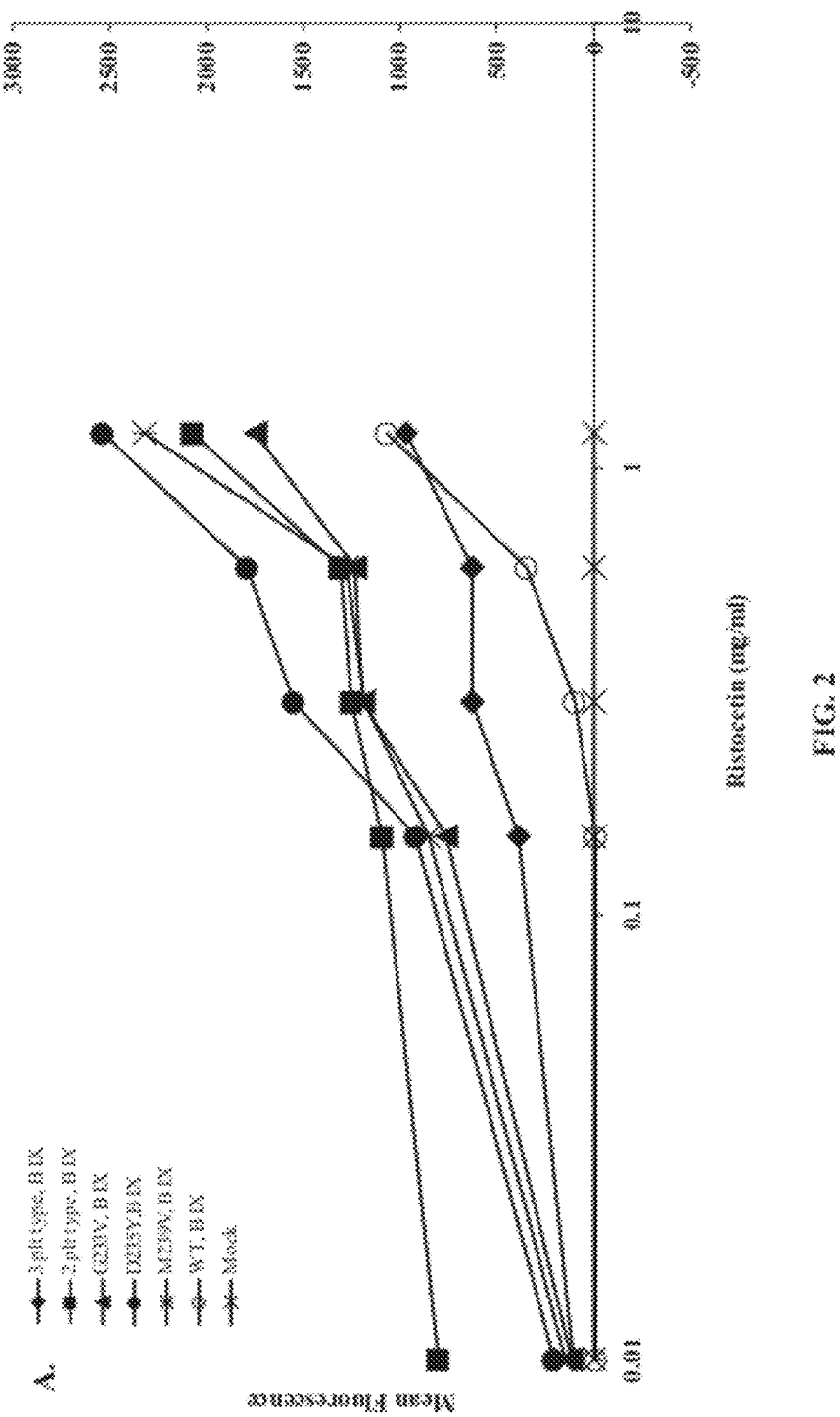
FIGS. 2A-C show the effect GPIbα mutations (single, double or triple.
Figure 2:
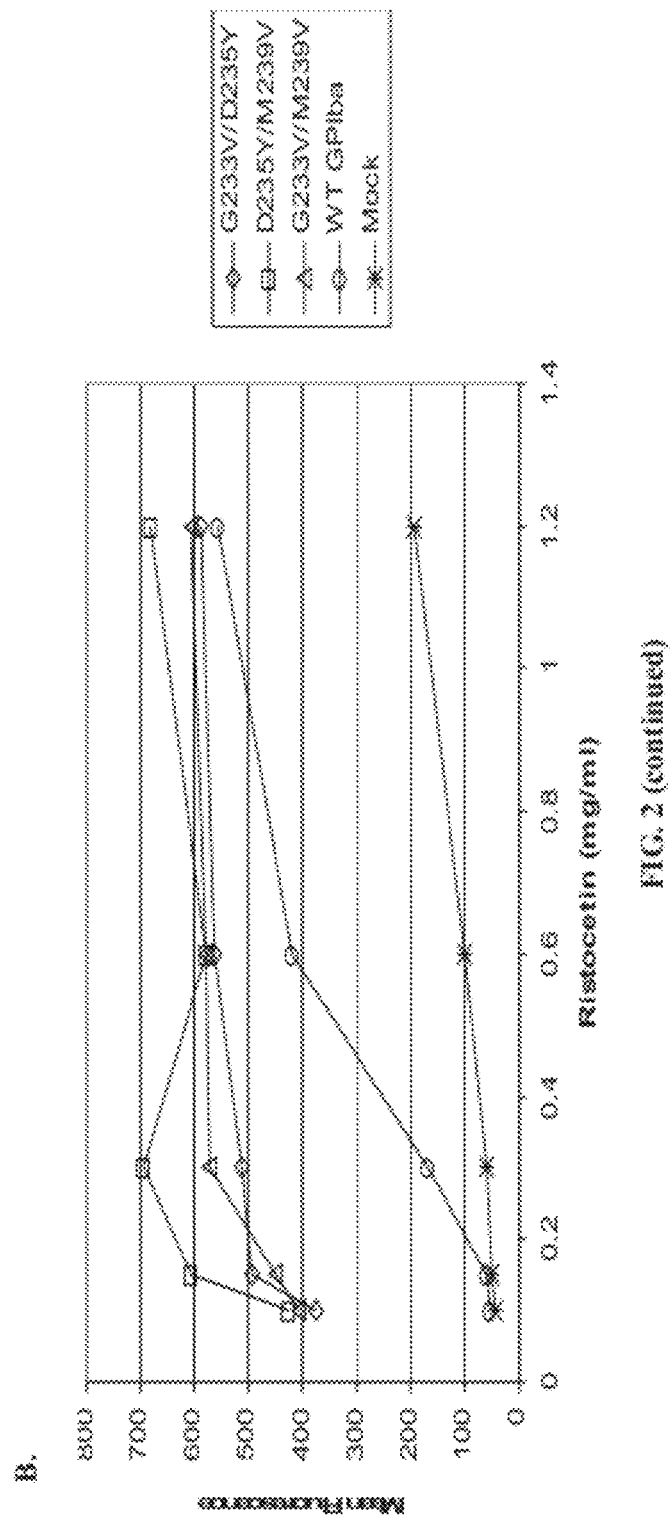
Figure 2:
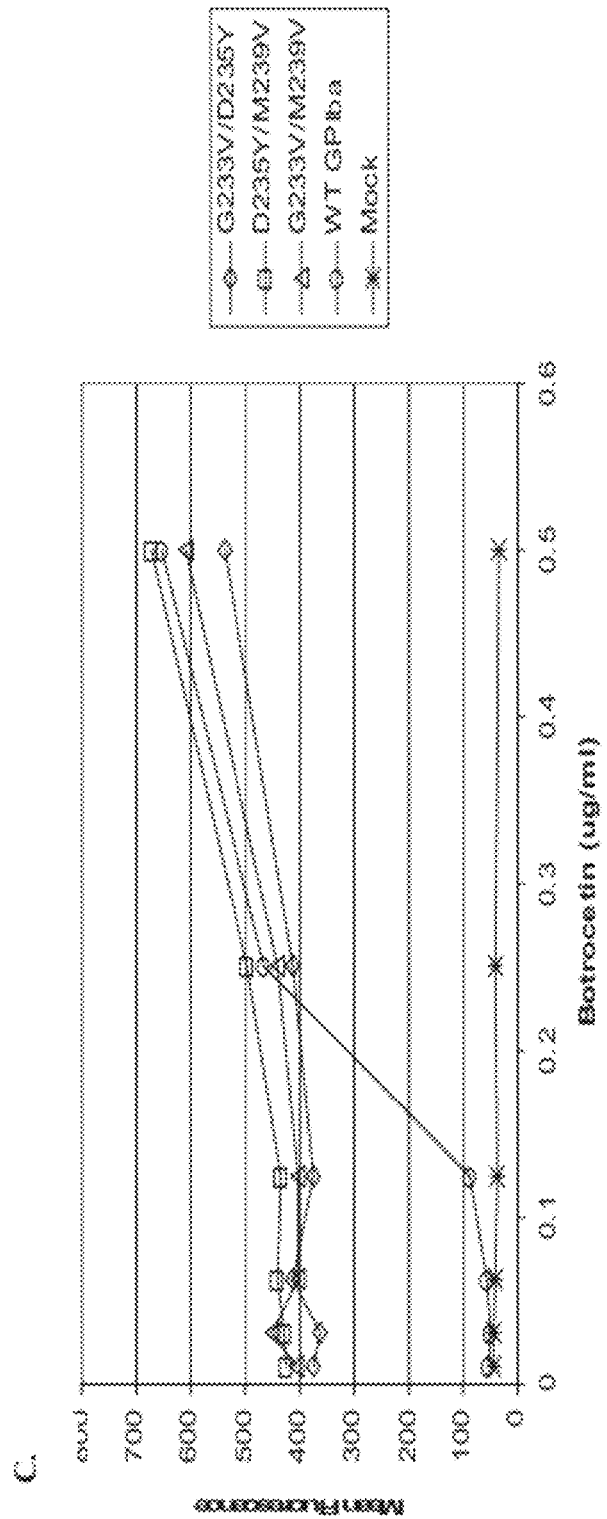

Results: As shown in FIG. 2A, mock transfected HEK-293T cells did not show any binding in the presence of ristocetin, while cells expressing wild-type GPIbα showed a concentration-dependent decrease in ristocetin binding after 1.2 mg/ml. HEK-293T cells expressing only one of the GPIbα mutations showed increased sensitivity even at low concentrations of ristocetin, which suggests that the binding is independent of ristocetin. Cells expressing two GPIbα mutations showed an extreme sensitivity to ristocetin or alternatively, an increased spontaneous binding that was independent of ristocetin. HEK-293T cells expressing the triple GPIbα mutation (i.e., G233V/D235Y/M239V), however, did not show increased sensitivity/spontaneous binding relative to the double mutants. As shown in FIG. 2B, each of the double mutants (i.e., G233V/M239V, G233V/D235Y or D235Y/M239V) showed comparable spontaneous binding relative to one another that was not significantly affected by ristocetin (i.e., ristocetinless). As expected the, wild-type control showed concentration-dependent increases in VWF:IbCo to ristocetin. As shown in FIG. 2C, VWF:IbCo is not affected by the type of platelet aggregation agonist, as none of the double mutants was significantly affected by botrocetin (i.e., botrocetinless). As expected, wild-type control showed concentration-dependent increases in VWF:IbCo to botrocetin.

Example 2

VWF Function in Patient Samples Using Mutant GPIbα in FACS

Methods: HEK293T cells were transiently transfected with a wild-type GPIbα construct or GPIbα encoding one of the double mutants, as described above. The cells were additionally transfected with the GPIbβ and GP-IX constructs. A group of HEK-293T cells were mock transfected, as describe above.

After forty-eight hours, the transfected cells were lifted from the plate with 3 mM EDTA, resuspended in assay buffer (i.e., 1×PBS containing 2% BSA) and counted. Trypsin was not used, as it potentially can cleave GPIbα from the cell surface. After counting, 1.75×10$^5$ cells were plated 96-well plate (Becton Dickinson; Franklin Lakes, N.J.) as a way of standardizing GPIbα on the plate surface, and the plate was then centrifuged at 2000 rpm for 5 minutes to pellet the cells. The supernatant was discarded.

HEK-293T cells expressing the GPIbα mutations were used in flow cytometry assays to test VWF binding, which was measured with a fluorescently labeled anti-VWF polyclonal antibody from Dako. A normal curve was developed using serial dilutions of reference plasma previously standardized against both the ISTH and WHO VWF standards based on the VWF:Ag international standard that is also standardized for VWF:RCo.

In one set of experiments, normal patient samples were used to determine whether the HEK-293T cells required all components of the platelet adhesion receptor or simply GPIbα. Normal patient samples were used. In another set of experiments, patient samples from normal individuals and individuals having VWD were used in the FACS assay as described above in Example 1.

Samples included 41 normals, 16 type-2M VWD, 5 type-2B VWD and 5 type-2A VWD plasma, Included therein were individuals with apparent type-2M VWD, but without clinical symptoms, and African Americans with a reduced VWF:RCo/VWF:Ag (RCo/Ag) ratio. Of the 16 type-2M VWD samples, 7 had markedly reduced VWF:IbCo (consistent with the VWF:RCo assay), and 9 had normal VWF:IbCo. African Americans with SNPs associated with reduced RCo/Ag ratios had VWF:IbCo assays that correlated with their VWF:Ag in contrast to the abnormal RCo/Ag ratios identified by standard assays. Type-2A individuals exhibited reduced VWF:IbCo assays and multimer size seemed to correlate with VWF:IbCo activity. Thus, measurement of VWF function using the VWF:IbCo assay more directly correlates with VWF function and avoids some of the pitfalls and functional variability of VWF:RCo assays.

Results: As shown in Table 2, GPIbβ and GP-IX are not required for surface expression of the mutant GPIbα, as FACS results from HEK-293T cells expressing multiple components of the plate adhesion receptor were not significantly different from cells expressing only GPIbα.

TABLE 2

Effect of GPIbα Having a Double Mutation With or Without the Other Platelet Adhesion Receptor Components in a FACS.

| Sample | Known VWF:RCo (IU/dL) | GPIbα (G233V/M239V), GPIbβ and IX | GPIbα | % Diff btw Transfections | % Diff. btw GPIbα, GPIbβ and IX & Known | % Diff. btw GPIbα & Known |
|---|---|---|---|---|---|---|
| ISTH 2 | 71 | 70.4 | 70.3 | 0.1 | 0.4 | 0.5 |
| ISTH 3 | 86 | 86.9 | 91.4 | 2.5 | 0.5 | 3.0 |
| CCNRP | 82 to 103 | 89.0 | 74.6 | 8.8 | 4.1 | 4.7 |
| Cntrl 3 | 65 | 64.4 | 52.1 | 10.5 | 0.5 | 11.0 |
| Cntrl 4 | 24.6 | 26.7 | 22.7 | 8.0 | 4.0 | 4.1 |
| JS | 0 | 0 | 0 | 0 | 0 | 0 |
| XX-01 | 200 | 136.4 | 119.5 | 6.6 | 18.9 | 25.2 |

ISTH = reference sample

As shown below in Table 3, the FACS assay resulted in VWF measurements comparable to a method used in clinical laboratories. Samples were normal individuals and individuals having VWD. Table 4 is similar to Table 3, except that the samples were from normal individuals and individuals having Type 2 VWD. Table 5 is also similar to Table 3, except that the samples were from individuals having Type 2M VWD.

TABLE 3

Summary of VWF:IbCo by FACS in Plasma Samples from African Americans and Caucasians with and without VWF Single Nucleotide Polymorphisms (SNPs).

| Sample | VWF:Ag 1 | VWF:RCo | Ratio 1 | VWF:Ag 2 | VWF:IbCo | Ratio 2 | Ratio 2/Ratio 1 |
|---|---|---|---|---|---|---|---|
| IN-09 | 215 | 104 | 0.484 | 167 | 131 | 0.781 | 0.608 |
| XX-22 | 193 | 140 | 0.725 | 152 | 240 | 1.579 | 1.244 |
| XX-24 | 278 | 225 | 0.809 | 233 | 240 | 1.029 | 0.863 |
| XX-27 | 195 | 130 | 0.667 | 186 | 147 | 0.788 | 0.753 |
| XX-29 | 85 | 74 | 0.871 | 79 | 104 | 1.313 | 1.222 |
| AT-09 | 103 | 69 | 0.670 | 88 | 78 | 0.886 | 0.756 |
| AT-13 | 71 | 72 | 1.014 | 72 | 89 | 1.226 | 1.251 |
| AT-14 | 257 | 248 | 0.965 | 231 | 233 | 1.009 | 0.906 |
| AT-17 | 225 | 95 | 0.422 | 188 | 144 | 0.768 | 0.641 |
| AT-18 | 225 | 195 | 0.867 | 186 | 155 | 0.834 | 0.689 |
| XX-21 | 85 | 92 | 1.082 | 90 | 72 | 0.801 | 0.844 |
| AT-06 | 154 | 176 | 1.143 | 150 | — | — | — |
| IN-15 | 122 | 85 | 0.697 | 83 | 140 | 1.685 | 1.146 |
| PB-06 | 86 | 88 | 1.023 | 78 | 137 | 1.755 | 1.594 |
| PB-14 | 234 | 211 | 0.902 | 238 | 197 | 0.831 | 0.843 |
| PB-17 | 109 | 93 | 0.853 | 104 | 68 | 0.649 | 0.620 |
| AT-16 | 82 | 94 | 1.146 | 73 | 94 | 1.284 | 1.143 |
| AT-19 | 164 | 151 | 0.921 | 147 | 126 | 0.859 | 0.771 |
| AT-42 | 86 | 69 | 0.802 | 70 | 64 | 0.902 | 0.739 |
| NO-53 | 243 | 252 | 1.037 | 239 | 159 | 0.666 | 0.655 |
| DT-08 | 68 | 71 | 1.044 | 58 | 62 | 1.064 | 0.910 |
| DT-01 | 88 | 107 | 1.216 | 91 | 82 | 0.906 | 0.937 |
| DT-06 | 82 | 79 | 0.963 | 83 | 82 | 0.981 | 0.995 |
| XX-04 | 96 | 109 | 1.135 | 86 | 128 | 1.481 | 1.334 |
| XX-06 | 129 | 149 | 1.155 | 111 | 128 | 1.148 | 0.993 |
| XX-13 | 124 | 169 | 1.363 | 114 | 186 | 1.638 | 1.503 |
| IN-13 | 103 | 92 | 0.893 | 100 | 88 | 0.887 | 0.859 |
| IN-22 | 96 | 110 | 1.146 | 104 | 65 | 0.627 | 0.678 |
| PB-09 | 88 | 78 | 0.886 | 100 | 77 | 0.767 | 0.870 |
| XX-03 | 106 | 136 | 1.283 | 103 | 160 | 1.551 | 1.511 |
| XX-12 | 137 | 183 | 1.336 | 128 | 189 | 1.437 | 1.380 |
| XX-14 | 115 | 163 | 1.417 | 109 | — | — | — |
| XX-15 | 123 | 137 | 1.114 | 159 | 122 | 0.768 | 0.992 |
| IN-01 | 209 | 220 | 1.053 | 149 | — | — | — |
| IN-03 | 71 | 68 | 0.958 | 68 | 54 | 0.801 | 0.762 |
| IN-07 | 95 | 85 | 0.895 | 77 | 76 | 0.995 | 0.802 |
| PB-01 | 84 | 77 | 0.917 | 82 | 71 | 0.862 | 0.805 |
| PB-04 | 155 | 162 | 1.045 | 146 | 105 | 0.722 | 0.678 |
| PB-20 | 107 | 114 | 1.065 | 91 | 95 | 1.046 | 0.855 |
| NO-23 | — | — | — | 143 | <1.1 | — | — |

1 = DT method (a clinical laboratory method)
2 = BRI method (Blood Research Institute method)
Shaded area = <0.81

TABLE 4

VWF:IbCo by FACS in Plasma from African Americans and Caucasians With/Without Type 2 VWD and Repeats.

| Sample | Race | VWD Phenotype | VWF Mutation | VWF:Ag | VWF:RCo | RCo/Ag | FACS1 | FACS1/Ag | FACS2 | FACS2/Ag |
|---|---|---|---|---|---|---|---|---|---|---|
| DB | AA | "2M" | 3 AA snps | 86 | 47 | 0.547 | 78 | 0.910 | 78 | 0.905 |
| MK0055 | AA | "2M" | P1467S | 257 | 36 | 0.140 | 214 | 0.833 | 184 | 0.718 |
| LJ | C | "2M" | 3 AA snps | 66 | 40 | 0.606 | 180 | 2.734 | 48 | 0.735 |
| IN0061 | | 2M | R1374C | 22 | 11 | 0.500 | 4 | 0.204 | 10 | 0.432 |
| RH | | 2B | R1308S | 43 | 37 | 0.860 | 67 | 1.558 | 67 | 1.557 |
| LB | | 2B | V1316M | 91 | 62 | 0.681 | 159 | 1.751 | 106 | 1.162 |
| SB | | 2B | V1316M | 27 | 12 | 0.444 | 36 | 1.347 | 25 | 0.914 |
| AJ | | 2B | H1268D | 21 | 17 | 0.810 | 31 | 1.484 | 41 | 1.959 |
| PB0068 | | 2B | R1306W | 23 | 13 | 0.565 | — | — | 25 | 1.065 |
| YG | | 2A | L1503P | 26 | 13 | 0.500 | — | — | 19 | 0.714 |
| AV | | 2A | G1579R | 46 | 16 | 0.348 | — | — | 1 | 0.028 |
| AT0021 | | 2A | M7401? | 31 | 12 | 0.387 | — | — | 18 | 0.574 |
| AT0032 | | 2A | I1628T | 120 | 32 | 0.267 | — | — | 103 | 0.586 |
| IA0001 | | 2A | R1597W | 33 | <10 | — | — | — | 8 | 0.247 |
| AT0017 | AA | NL | 3 AA snps | 225 | 95 | 0.422 | 144 | 0.641 | 156 | 0.695 |
| XX0027 | AA | NL | 3 AA snps | 195 | 130 | 0.677 | 147 | 0.753 | 116 | 0.595 |
| XX0004 | C | NL | — | 96 | 109 | 1.135 | 128 | 1.334 | 114 | 1.183 |
| XX0013 | C | NL | — | 124 | 169 | 1.363 | 186 | 1.503 | 105 | 0.843 |
| PB0014 | AA | NL | — | 234 | 211 | 0.902 | 197 | 0.843 | 213 | 0.909 |
| AT0042 | AA | NL | — | 86 | 69 | 0.802 | 64 | 0.739 | 91 | 1.056 |

AA = African American
C = Caucasian
NL = normal
"2M" = apparent type 2M

TABLE 5

VWF Function in Plasma from African Americans and Caucasians With/Without Type 2 M VWD.

| Sample | Race | VWD Phenotype | VWF Mutation | VWF:Ag 1 | VWF:RCo 1 | RCo/Ag 1 | FACS2 | FACS2/Ag |
|---|---|---|---|---|---|---|---|---|
| TB | C | "2M" | — | 127 | 87 | 0.69 | 87 | 0.69 |
| DB | AA | "2M" | 3 AA snps | 86 | 47 | 0.55 | 78 | 0.91 |
| AC | C | 2M | G13242S | 95 | 13 | 0.14 | <1.1 | — |
| BF | — | 2M | I1416T (new) | 89 | 31 | 0.35 | 36 | 0.41 |
| MG | H | 2M | I1425F | 45 | 16 | 0.36 | >1.1 | — |
| LG | C | 2M | E1359K | 67 | 37 | 0.55 | 27 | 0.41 |
| GI | — | 2M | D1283H (new) | 16 | 4 | 0.25 | <1.1 | — |
| KJ | C | 2M | — | | 12 | 3 | 0.25 | <1.1 | — |
| LJ | AA | "2M" | 3 AA snps | 66 | 40 | 0.61 | 180 | 2.73 |
| BM | C | 2M | I1426T | 156 | 43 | 0.28 | 93 | 0.60 |
| AR | — | 2M | R1374L | 48 | 10 | 0.21 | <1.1 | — |
| DR | AA | "2M" | R1342C; I1343V; 1301-3103 del; and R2185Q | 38 | 12 | 0.32 | 37 | 0.97 |
| MK0038 | C | 2M | R1392-Q1402 del | 47 | 11 | 0.23 | <1.1 | — |
| IN0061 | C | 2M | R1374C | 22 | 11 | 0.50 | 4 | 0.20 |
| MK0055 | AA | "2M" | P1467S | 257 | 36 | 0.14 | 214 | 0.83 |
| MK0058 | AA | "2M" | P1467S | 265 | 68 | 0.14 | 194 | 0.73 |

AA = African American
C = Caucasian
H = Hispanic

Figure 4:
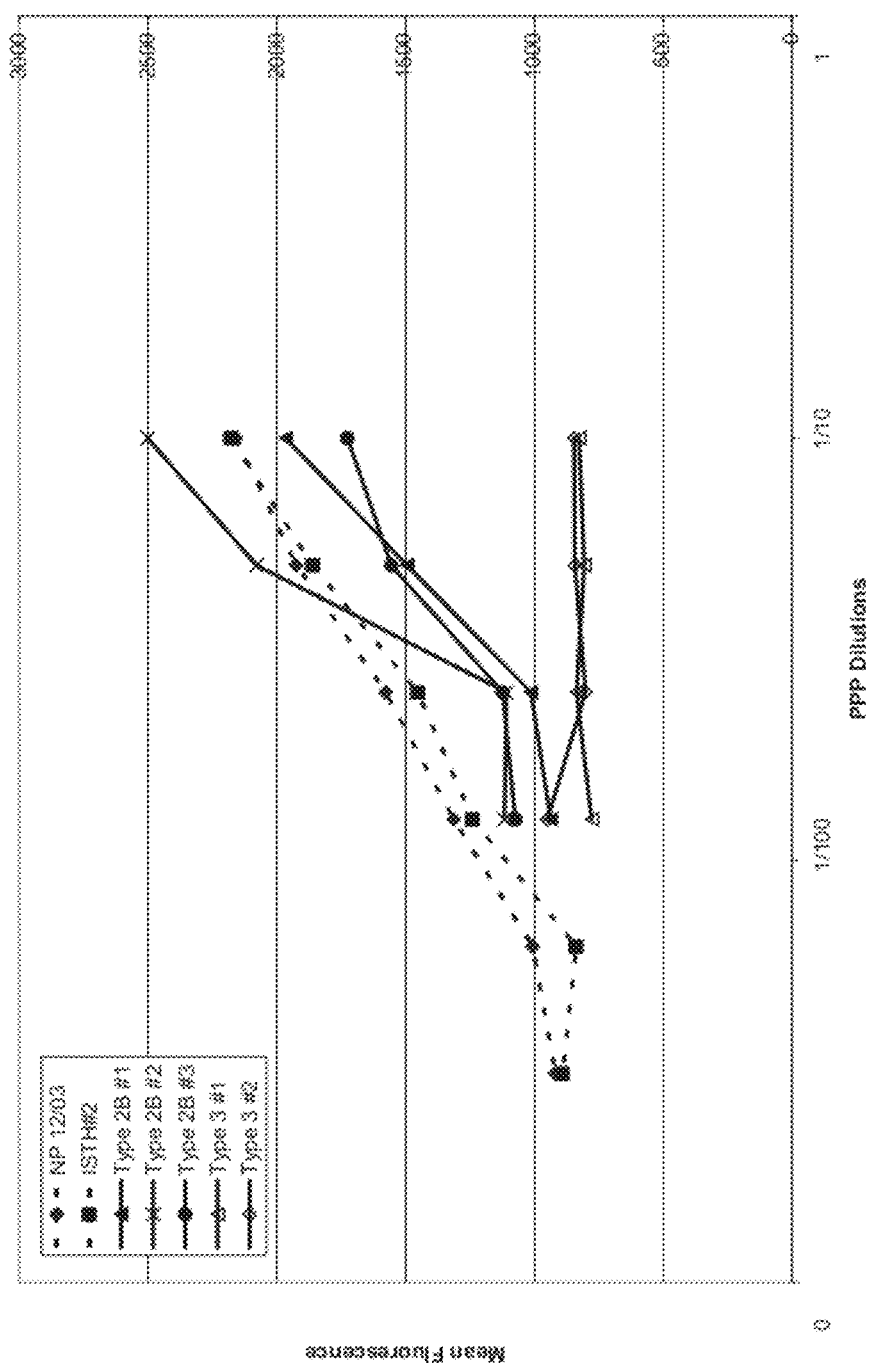
FIG. 4 shows an FACS assay with additional samples from individuals having type 2B VWD, which has gain-of-function VWF mutations (y-axis is mean fluorescence and x-axis is platelet poor plasma (PPP) dilutions).

Results: As shown in FIG. 4, individuals with normal VWF showed a typical increase in mean fluorescence with lower dilutions of their plasma. As expected, individuals with Type 3 VWD showed change in mean fluorescence because their plasma has low or no VWF.

Figure 5:
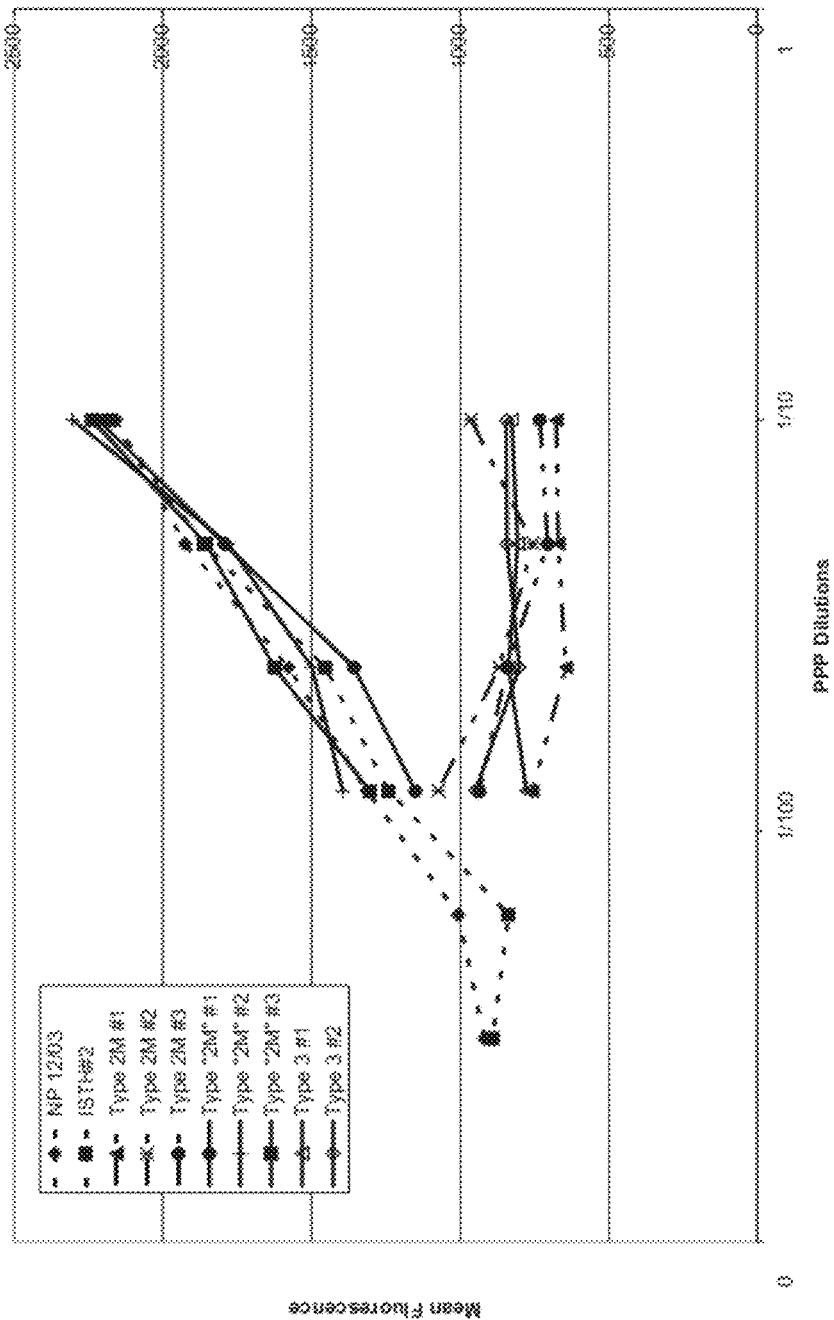
FIG. 5 shows a FACS assay with additional samples from individuals having type 2M VWD, which has low GPIb binding, and apparent type 2M VWD, which has low VWF:RCo/VWF:Ag, yet normal levels of VWF (y-axis is mean fluorescence and x-axis is platelet poor plasma (PPP) dilutions).

As shown in FIG. 5, individuals with Type 2B VWD showed a much earlier increase in mean fluorescence when compared to normals, starting at very high dilutions of their plasma (i.e., >1/100). Type 2B VWD is characterized as having gain-of-function mutations. Again, individuals with Type 3 VWD showed no reaction in the assay.

Figure 6:
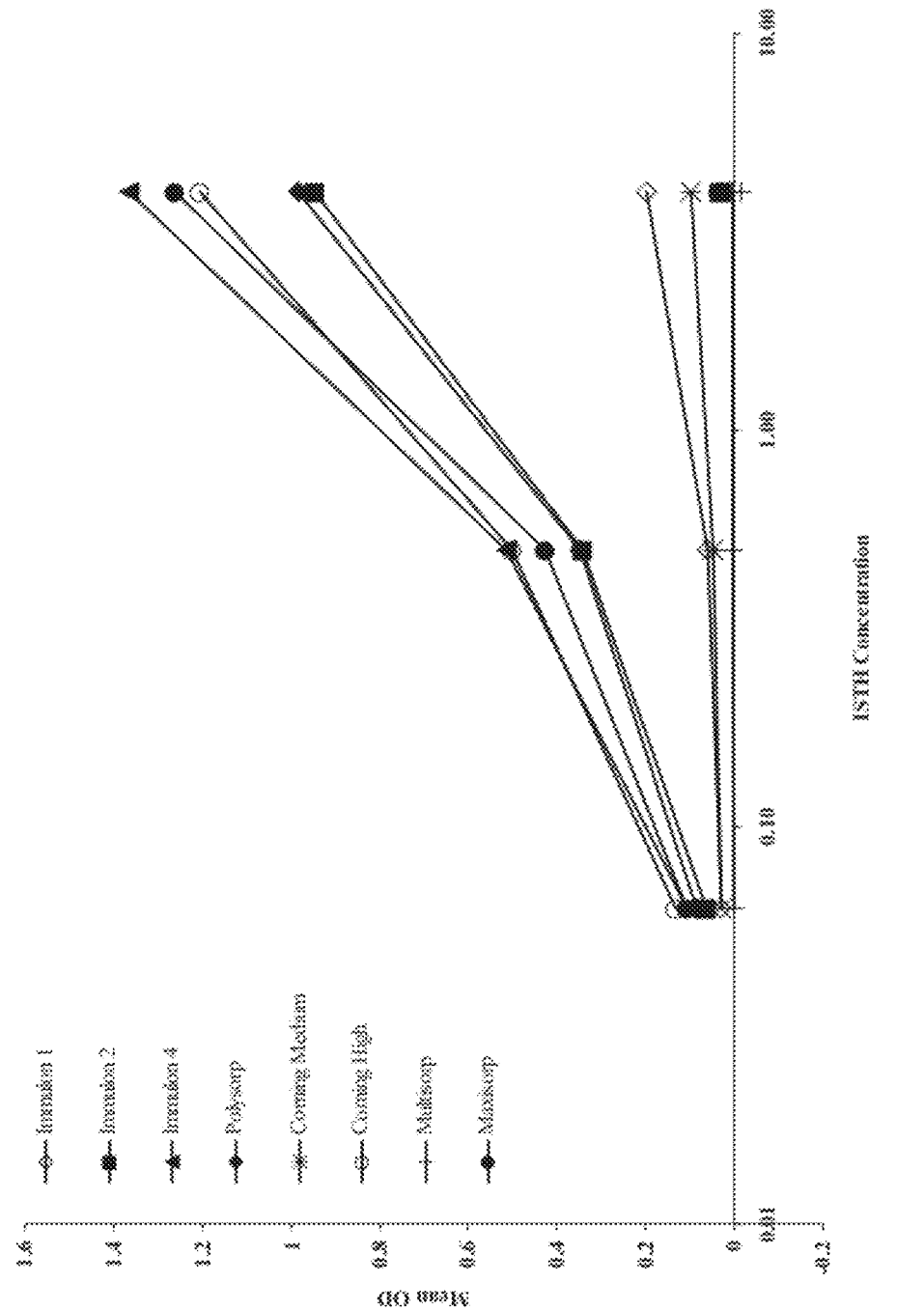
FIG. 6 shows the effect of charge on the solid-phase surface during an ELISA with immobilized GPIbα having two platelet-type, pseudo VWD mutations (y-axis is mean fluorescence and x-axis is ISTH (a standard) concentration in U/dL).

As shown in FIG. 6, individuals with Type 2M VWD showed no increase in mean fluorescence when compared to normals. Type 2M VWD is characterized by defective VWF that does not interact with GPIbα. Individuals with apparent Type 2M ("2M") showed a much earlier increase in mean fluorescence when compared to normals, starting at very high dilutions of their plasma (i.e., >1/100). Apparent Type 2M is characterized by low VWF:RCo/VWF:Ag, yet normal levels of VWF. Again, individuals with Type 3 VWD showed no reaction in the assay.

Example 3

Mutant GPIbα Function in ELISA

S2 cells (Invitrogen) were stably transfected with a mutant GPIbα construct, a wild-type GPIbα construct and a GP-IX construct. In some experiments, S2 cells were transfected with GPIbα constructs having a C65A mutation and ΔTM290 mutation. The C65A mutation removed a cysteine that could potential allow dimerization of GPIbα; and the ΔTM290 mutation removed the transmembrane region so that the expressed protein was excreted.

Briefly, the constructs were cloned into a pMT/Bip/V5-His:GPIbαC65A,D235Y,M239V ΔTM290 or pMT/Bip/V5-His:GPIbα C65A ΔTM290 secretion vector (Invitrogen). On day 1, S2 cells were counted and seeded into a 35 mm dish or a well of a 6 well plate at $3\times10^6$ cells in 3 ml of complete medium (Ex-Cell 420+10% FBS+7 mM L-Glutamine). The cells were allowed to grow 6-8 hours at 28° C. The following was added to one set of tubes: Solution A, which contained 36 μl of 2M $CaCl_2$, 19 μg of plasmid DNA (purified with Qiagen Maxi Kit; Qiagen; Valencia, Calif.), 1 μg pCoBlast (selection vector) and dd$H_2O$ up to 300 μl. The following was added to another set of tubes: Solution B, which contained 300 μl of 2×HEPES buffered saline. Solution A was slowly added dropwise to solution B while gently vortexing. The combined solutions then were incubated at room temperature for 30-40 minutes until a fine precipitate formed.

The mixed solution was added dropwise to the plated cells while gently swirling the plate. The cells were then incubated overnight at 28° C. (about 16-24 hours).

The next day, the transfection solution was removed and replaced with 3 ml of fresh complete medium and incubated at 28° C. without $CO_2$. On day 5, the cells were resuspended cells and transferred to a 15 cc conical tube, centrifuged at 2400 rpm for 2 minutes. The medium was decanted, and the cells were resuspended in 3 ml of stable medium (complete medium +25 μg/ml Blastidin-S) and plated in a new dish or well.

Selection began on week 2. As done on Day 5, the selection medium was replaced every 3-4 days with 3 ml fresh selection medium. Selection and expansion continued through week 3. During this time, the cells were resuspended, transferred to 15 cc conical tubes, and centrifuged at 2400 rpm for 2 minutes. The media as decanted, and the cells were resuspended in 5 ml of selector media and plated in new T25 flask. After 4 days, the cells were expanded from 1 T25 to 2 T25 flasks.

Expansion and freezing stocks began on week 4. Cells were expanded from the T25 flasks to T75 flasks ($3\times10^6$ cells/ml medium). T75 flasks received 15 ml medium, which was about $45\times10^6$ cells. The remaining cells (about $2\times10^7$ cells/vial) were frozen and stored in liquid nitrogen.

Induction of the cells in the T75 flasks began on week 5. Cells were resuspended, transferred to a 15 cc conical tube for counting and centrifuged. $45\times10^6$ cells were resuspended 15 ml induction medium (stable medium +500 μM $CuSO_4$) and transferred to T75 flasks. The cells were then incubated 4 days at 28° C., the supernatant having secreted GPIbα was harvested.

Figure 3:
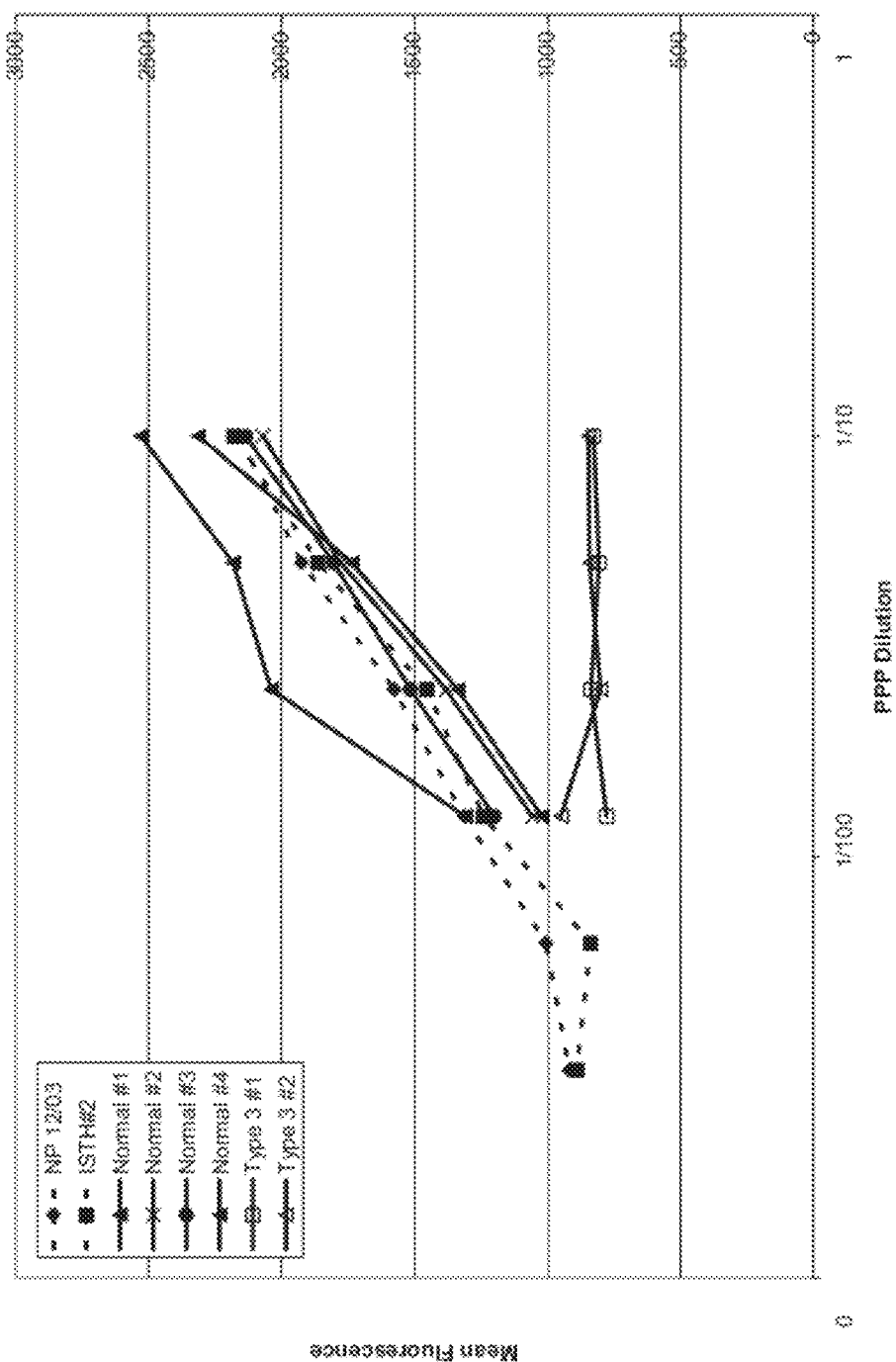
FIG. 3 shows an FACS assay with GPIbα having two platelet-type, pseudo VWD mutations using samples from control individuals and with type 3 VWD, which has low to undetectable VWF (y-axis is mean fluorescence and x-axis is platelet poor plasma (PPP) dilutions).

As shown Table 6 and FIG. 3, various solid-phase surfaces were first tested for the ELISA assays. Table 6 shows that the surface density of GPIbα was affected by the surface charge of the solid-phase surface; whereas FIG. 3 shows that different solid-phase surfaces coated with GPIbα having a double mutation affected VWF binding. Solid-phase surface charge appeared to affect GPIbα/VWF binding, suggesting that any solid-phase surface should first be tested for it ability (1) to provide a uniform density of GPIbα and (2) to permit VWF to bind to the GPIbα. After considering both Table 6, and FIG. 3, Immulon 4 HBX Plates worked best and were used thereafter.

TABLE 6

Effect of Various Solid-Phase Surfaces on Concentration of GPIbα Double Mutation (G233V/M239V) (same samples on different plates).

| Solid-Phase Surface | Characteristic of the Surface | Calculated GPIbα concentration |
|---|---|---|
| Immulon 1 | Hydrophobic | 635.1 |
| Immulon 2 | Hydrophobic | 370.8 |
| Immulon 4 | Maximum | 383.7 |
| Polysorp | Hydrophobic | 321.7 |
| Corning Medium | Hydrophobic | 576.8 |
| Corning High | Ionic and/or Hydrophobic | 414.7 |
| Multisorb | Polar Molecules | No binding |
| Maxisorb | Hydrophobic/Hydrophilic | 408.5 |

An Immulon 4 HBX Plate (Thermo Scientific; Waltham, Mass.) was coated with anti-GPIbα monoclonal antibody 142.16 (Blood Research Institute) at a concentration of 5 μg/ml, which was then incubated overnight at 4° C. The plate was blocked with PBS containing 1% BSA for 1 hour at room temperature. Nickel-purified S2-expressed proteins—GPIbα C65A, D235Y, M239V and ΔTM290—were diluted in PBS containing 1% BSA and incubated on the anti-GPIbα antibody-coated plate for 1 hour at 37° C. See, Celikel et al., supra.

PPP from controls or individuals having VWD was diluted 1:50 in PBS containing 1% BSA and serially diluted 1:2 to a final dilution of 1:100. Diluted PPP was added to the plate and incubated for 1 hour at 37° C. ISTH Lot#3 was again used as a standard, with curve dilutions starting at 1:25 in substrate buffer, which was then serially diluted 1:2 to a final dilution of 1:1600. 2 μg/ml biotinylated AVW-1 and AVW-15 (Blood Research Institute) were added to the plate and incubated for 30 minutes at 37° C. Finally, streptavidin-conjugated alkaline phosphatase (Jackson ImmunoResearch Laboratories, Ltd.; West Grove, Pa.), diluted 1:5000 in substrate buffer, was added to the plate and incubated for 30 minutes at 37° C. p-Nitrophenyl Phosphate (PNPP; Invitrogen), an alkaline phosphate substrate, was diluted 1:100 in substrate buffer and added to the plate. The plate was read at 405/650 nm on a plate reader. The plate was washed three times between each step with PBS containing 0.05% Tween-20.

Results: As shown in Tables 7 and 8, individuals with normal VWF showed similar ELISA results whether ristocetin was added to the assay or not. In addition, the ELISA assay resulted in VWF measurements comparable to a method used in clinical laboratories

TABLE 7

Summary of VWF:IbCo by ELISA in Plasma Samples from African Americans and Caucasians with and without VWF Single Nucleotide Polymorphisms (SNPs).

| Subject | VWF:Ag | IbCo ELISA | Ristocetin ELISA | IbCo/ VWF:Ag | Ris/ VWF:Ag | Clinical VWF:Ag | VWF:RCo | VWF:RCo/ VWF:Ag |
|---|---|---|---|---|---|---|---|---|
| ISTH 3 A | 121.25 | 109.4 | 127.3 | 0.90 | 1.05 | 106 | 86 | 0.81 |
| ctrl 5 (70%) | 75.62 | 68.97 | 69.68 | 0.91 | 0.92 | 74.2 | 60.2 | 0.81 |
| ctrl 6 (35%) | 32.28 | 31.12 | 28.76 | 0.96 | 0.89 | 37.1 | 30.1 | 0.81 |
| CCNRP 7122 A | 94.56 | 84.6 | 73.34 | 0.89 | 0.78 | 114 | 71 | 0.62 |
| ISTH 3 B | 96.71 | 99.71 | 104.05 | 1.03 | 1.08 | 106 | 86 | 0.81 |

TABLE 7-continued

Summary of VWF:IbCo by ELISA in Plasma Samples from African Americans and Caucasians with and without VWF Single Nucleotide Polymorphisms (SNPs).

| Subject | VWF:Ag | IbCo ELISA | Ristocetin ELISA | IbCo/ VWF:Ag | Ris/ VWF:Ag | Clinical VWF:Ag | VWF:RCo | VWF:RCo/ VWF:Ag |
|---|---|---|---|---|---|---|---|---|
| MK0038 | 33.44 | 1.41 | 14.16 | 0.04 | 0.42 | 47 | 11 | 0.23 |
| XX0017 | 139.5 | 157.35 | 169.5 | 1.13 | 1.22 | 206 | 200 | 0.97 |
| JS | 0 | 0.5 | 0.99 | 0.00 | 0.00 | <1 | <10 | 0.00 |
| ctrl 8 (30%) | 23.84 | 26.96 | 23.58 | 1.13 | 0.99 | 31.8 | 25.8 | 0.81 |
| ISTH 3 C | 85.14 | 94.42 | 90.48 | 1.11 | 1.06 | 106 | 86 | 0.81 |
| CCNRP 7122 B | 59.61 | 60.64 | 55.44 | 1.02 | 0.93 | 114 | 71 | 0.62 |
| AT0068 | 70.4 | 59.18 | 31.47 | 0.84 | 0.45 | 99 | 57 | 0.58 |

TABLE 8

Summary of VWF:IbCo by ELISA in Plasma Samples from African Americans and Caucasians with and without VWF Single Nucleotide Polymorphisms (SNPs).

| Subject | Clinical VWF:Ag | BRI VWF:Ag | Clinical VWF:RCo | IbCo ELISA | Ristocetin ELISA | Clinical VWF:RCo/ VWF:Ag | IbCo ELISA/BRI VWF:Ag |
|---|---|---|---|---|---|---|---|
| AA w/1380 + 1435 + 1472 | | | | | | | |
| HN | 334 | 228 | 165 | 165 | — | 0.494 | 0.725 |
| XX | 278 | 228 | 225 | 235 | 222 | 0.809 | 1.029 |
| AT | 257 | 309 | 248 | 234 | 220 | 0.965 | 0.759 |
| AT | 225 | 159 | 198 | 149 | 152 | 0.880 | 0.932 |
| AT | 225 | 172 | 95 | 67 | 106 | 0.422 | 0.393 |
| IN | 215 | 179 | 104 | 77 | 73 | 0.484 | 0.429 |
| XX | 193 | 200 | 140 | 123 | 154 | 0.725 | 0.616 |
| NO | 179 | 178 | 180 | 171 | — | 1.006 | 0.960 |
| AT | 103 | 83 | 69 | 58 | 64 | 0.670 | 0.701 |
| XX | 85 | 67 | 74 | 73 | 57 | 0.871 | 1.095 |
| AT | 71 | 65 | 72 | 70 | 53 | 1.014 | 1.077 |
| HN | 67 | 77 | 54 | 54 | — | 0.806 | 0.704 |
| AA w/1472 alone | | | | | | | |
| NO | 259 | 209 | 224 | 151 | 213 | 0.865 | 0.723 |
| XX | 195 | 129 | 130 | 118 | 132 | 0.667 | 0.910 |
| XX | 185 | 143 | 154 | 143 | 183 | 0.832 | 1.001 |
| XX | 167 | 172 | 170 | 123 | 198 | 1.018 | 0.714 |
| NO | 166 | 151 | 175 | 155 | — | 1.054 | 1.025 |
| IN | 153 | 123 | 146 | 120 | 55 | 0.954 | 0.970 |
| NO | 144 | 141 | 85 | 92 | — | 0.590 | 0.652 |
| DT | 141 | — | 121 | — | — | 0.858 | — |
| HN | 139 | — | 98 | — | — | 0.705 | — |
| XX | 137 | 112 | 123 | 90 | 151 | 0.898 | 0.801 |
| HN | 136 | 136 | 113 | 106 | — | 0.831 | 0.784 |
| XX | 122 | 89 | 85 | 75 | — | 0.697 | 0.839 |
| XX | 116 | 103 | 89 | 82 | 81 | 0.767 | 0.793 |
| XX | 110 | 104 | 91 | 100 | 62 | 0.827 | 0.967 |
| IN | 108 | 107 | 101 | 86 | 94 | 0.935 | 0.800 |
| AT | 99 | 91 | 57 | 50 | 25 | 0.576 | 0.550 |
| DT | 98 | 89 | 85 | 79 | 85 | 0.867 | 0.885 |
| AT | 84 | 96 | 79 | 82 | 63 | 0.940 | 0.856 |
| AA w/no SNPs | | | | | | | |
| NO | 243 | 237 | 252 | 217 | — | 1.037 | 0.917 |
| PB | 234 | 192 | 211 | 110 | 83 | 0.902 | 0.576 |
| DT | 224 | 185 | 167 | 190 | — | 0.746 | 1.025 |
| AT | 199 | 178 | 193 | 177 | — | 0.970 | 0.993 |
| NO | 195 | 179 | 220 | 207 | 233 | 1.128 | 1.160 |
| AT | 164 | 132 | 151 | 98 | 96 | 0.921 | 0.743 |
| AT | 154 | 139 | 176 | 159 | 135 | 1.143 | 1.143 |
| IN | 122 | 76 | 85 | 68 | 74 | 0.697 | 0.897 |
| PB | 109 | 91 | 93 | 76 | 63 | 0.853 | 0.832 |
| PB | 86 | 63 | 88 | 64 | 52 | 1.023 | 1.025 |
| AT | 86 | 107 | 97 | 68 | 63 | 1.128 | 0.633 |
| AT | 86 | 57 | 69 | 60 | 56 | 0.802 | 1.055 |
| XX | 85 | 79 | 92 | 65 | 44 | 1.082 | 0.817 |
| AT | 82 | 93 | 94 | 70 | 49 | 1.146 | 0.750 |

TABLE 8-continued

Summary of VWF:IbCo by ELISA in Plasma Samples from African Americans and Caucasians with and without VWF Single Nucleotide Polymorphisms (SNPs).

| Subject | Clinical VWF:Ag | BRI VWF:Ag | Clinical VWF:RCo | IbCo ELISA | Ristocetin ELISA | Clinical VWF:RCo/ VWF:Ag | IbCo ELISA/BRI VWF:Ag |
|---|---|---|---|---|---|---|---|
| C w/1380 + 1435 + 1472 | | | | | | | |
| PB | 180 | 144 | 149 | 122 | 115 | 0.828 | 0.842 |
| IN | 94 | 91 | 84 | 68 | 79 | 0.894 | 0.747 |
| C w/1472 alone | | | | | | | |
| XX | 206 | 254 | 200 | 266 | 251 | 0.971 | 1.050 |
| IN | 192 | 137 | 144 | 133 | 126 | 0.750 | 0.973 |
| DT | 174 | 148 | 137 | 165 | 127 | 0.787 | 1.119 |
| IN | 171 | 106 | 122 | 94 | 127 | 0.713 | 0.888 |
| PB | 129 | 102 | 85 | 76 | 66 | 0.659 | 0.751 |
| IN | 111 | 88 | 99 | 76 | 78 | 0.892 | 0.861 |
| XX | 97 | 67 | 89 | 82 | 80 | 0.918 | 1.224 |
| HN | 94 | 103 | 82 | 82 | — | 0.872 | 0.791 |
| IN | 91 | 65 | 88 | 58 | 51 | 0.967 | 0.902 |
| C w/no SNPs | | | | | | | |
| PB | 289 | 313 | 256 | 309 | 292 | 0.886 | 0.988 |
| IN | 237 | 171 | 255 | 154 | 275 | 1.076 | 0.901 |
| IN | 187 | 165 | 138 | 124 | 144 | 0.738 | 0.753 |
| XX | 129 | 121 | 149 | 90 | 112 | 1.155 | 0.745 |
| XX | 124 | 128 | 169 | 137 | 127 | 1.363 | 1.073 |
| IN | 103 | 82 | 92 | 67 | 78 | 0.893 | 0.815 |
| IN | 100 | 71 | 91 | 68 | 72 | 0.910 | 0.957 |
| XX | 96 | 93 | 109 | 132 | 103 | 1.135 | 1.425 |
| IN | 96 | 86 | 110 | 94 | 87 | 1.146 | 1.086 |
| XX | 94 | 77 | 101 | 74 | 83 | 1.074 | 0.972 |
| XX | 94 | 100 | 86 | 88 | 93 | 0.915 | 0.875 |
| DT | 88 | 90 | 107 | 91 | 83 | 1.216 | 1.008 |
| PB | 88 | 79 | 78 | 50 | 54 | 0.886 | 0.628 |
| IN | 85 | 61 | 77 | 58 | 57 | 0.906 | 0.961 |
| IN | 85 | 74 | 82 | 65 | 56 | 0.965 | 0.872 |
| PB | 83 | 80 | 88 | 60 | 51 | 1.060 | 0.742 |
| DT | 82 | 73 | 79 | 65 | 63 | 0.963 | 0.891 |
| PB | 74 | 52 | 69 | 53 | 34 | 0.932 | 1.017 |
| DT | 68 | 57 | 71 | 55 | 56 | 1.044 | 0.956 |
| XX | 58 | 54 | 61 | 52 | 49 | 1.052 | 0.958 |

AA = African American
C = Caucasian

Thus, measurement of VWF function using a VWF:IbCo FACS or ELISA assay more directly correlates with VWF function and avoids some of the pitfalls and functional variability observed with VWF:RCo assays.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. An isolated GPIbα polypeptide or functional fragment thereof, comprising an amino acid sequence that has at least 90% sequence identity to residues 1-290 of SEQ ID NO:11 and that includes at least two mutations relative to residues 1-290 of SEQ ID NO:11, wherein one of the mutations is D235Y;
wherein the isolated GPIbα polypeptide or fragment is capable of forming a complex with von Willebrand factor (VFW).

2. The isolated GPIbα polypeptide or functional fragment of claim 1, wherein the second mutation in the amino acid sequence having at least 90% sequence identity to residues 1-290 of SEQ ID NO:11 is selected from the group consisting of G233V and M239V.

3. The isolated GPIbα polypeptide or functional fragment of claim 2, wherein the amino acid sequence having at least 90% sequence identity to residues 1-290 of SEQ ID NO:11 includes the three mutations D235Y/G233V/M239V.

4. The isolated GPIbα polypeptide or functional fragment of claim 1, wherein the amino acid sequence having at least 90% sequence identity to residues 1-290 of SEQ ID NO:11 includes a mutation to prevent dimerization with a second GPIbα polypeptide.

5. The isolated GPIbα polypeptide or functional fragment of claim 1, having a C65A mutation.

6. The isolated GPIbα polypeptide or functional fragment of claim 1, wherein the amino acid sequence having at least 90% sequence identity to residues 1-290 of SEQ ID NO:11 lacks a transmembrane region.

7. The isolated GPIbα polypeptide or functional fragment of claim 1, wherein the polypeptide or functional fragment is coated to a solid-phase surface.

8. The isolated GPIbα polypeptide or functional fragment of claim 7, wherein the amino acid sequence having at least 90% sequence identity to residues 1-290 of SEQ ID NO:11 has one or both of a G233V or an M239V mutation.

9. The isolated GPIbα polypeptide or functional fragment of claim 8, wherein the polypeptide or functional fragment is further modified to prevent dimerization with a second GPIbα polypeptide, lacks a transmembrane region or both.

10. The isolated GPIbα polypeptide or functional fragment of claim 8, wherein the polypeptide is coated to a solid-phase surface using an anti-GPIbα monoclonal antibody.

11. The isolated GPIbα polypeptide or functional fragment of claim 10, wherein the amino acid sequence having at least 90% sequence identity to residues 1-290 of SEQ ID NO:11 has a C65A mutation.

12. The isolated GPIbα polypeptide or functional fragment of claim 10, wherein the polypeptide lacks a transmembrane region.

13. An ELISA assay kit for measuring vonWillebrand activity, wherein the kit contains the GPIbα polypeptide or functional fragment of claim 1.

14. The ELISA assay kit of claim 13, wherein the polypeptide or functional fragment is coated to a solid-phase surface.

15. A method for diagnosing vonWillebrand disease (VWD) comprising:
contacting a biological sample from an individual suspected of having VWD with the polypeptide or functional fragment of claim 1; and
detecting a complex between the polypeptide or functional fragment and vonWillebrand Factor (VWF).

16. The method of claim 15, wherein the method is a vonWillebrand Factor activity assay and the method is performed in the presence of a platelet aggregation agonist.

17. The method of claim 16, wherein the method is a vonWillebrand Factor activity assay and the method is performed in the presence of from about 0 mg/ml to about 1.2 mg/ml of Ristocetin.

18. An ELISA assay kit for measuring vonWillebrand activity, wherein the kit contains the GPIbα polypeptide or functional fragment of claim 2.

19. The ELISA assay kit of claim 18, wherein the wherein the polypeptide or functional fragment is coated to a solid-phase surface.

20. An ELISA assay kit for measuring vonWillebrand activity, wherein the kit contains the GPIbα polypeptide or functional fragment of claim 3.

21. The ELISA assay kit of claim 20, wherein the wherein the polypeptide or functional fragment is coated to a solid-phase surface.

22. A method for diagnosing vonWillebrand disease comprising:
contacting a biological sample from an individual suspected of having VWD with the polypeptide or functional fragment of claim 2; and
detecting a complex between the polypeptide or functional fragment and vonWillebrand Factor (VWF).

23. The method of claim 22, wherein the method is a vonWillebrand Factor activity assay and the method is performed in the presence of a platelet aggregation agonist.

24. The method of claim 22, wherein the method is a vonWillebrand Factor activity assay and the method is performed in the presence of from about 0 mg/ml to about 1.2 mg/ml of Ristocetin.

25. A method for diagnosing vonWillebrand disease, wherein the method uses the polypeptide or functional fragment of claim 3.

26. The method of claim 25, wherein the method is a vonWillebrand Factor activity assay and the method is performed in the presence of a platelet aggregation agonist.

27. The method of claim 25, wherein the method is a vonWillebrand Factor activity assay and the method is performed in the presence of from about 0 mg/ml to about 1.2 mg/ml of Ristocetin.

* * * * *

UNITED STATES PATENT AND TRADEMARK OFFICE
CERTIFICATE OF CORRECTION

PATENT NO.        : 9,046,535 B2                                      Page 1 of 1
APPLICATION NO.   : 13/421217
DATED             : June 2, 2015
INVENTOR(S)       : Robert Montgomery It is certified that error appears in the above-identified patent and that said Letters Patent is hereby corrected as shown below:

In the specification,

Column 12, line 6 - "Mims" should be "Mirus"

Signed and Sealed this
Thirteenth Day of October, 2015

Michelle K. Lee
*Director of the United States Patent and Trademark Office*